United States Patent
Kim

(10) Patent No.: US 10,662,223 B2
(45) Date of Patent: *May 26, 2020

(54) COMPOSITION FOR ORGAN, TISSUE, OR CELL TRANSPLANTATION, KIT, AND TRANSPLANTATION METHOD

(71) Applicant: GemVax & KAEL Co., Ltd., Daejeon (KR)

(72) Inventor: Sang Jae Kim, Seoul (KR)

(73) Assignee: GemVax & KAEL Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/307,632

(22) PCT Filed: May 28, 2014

(86) PCT No.: PCT/KR2014/004752
§ 371 (c)(1),
(2) Date: Oct. 28, 2016

(87) PCT Pub. No.: WO2015/167067
PCT Pub. Date: Nov. 5, 2015

(65) Prior Publication Data
US 2017/0058001 A1    Mar. 2, 2017

(30) Foreign Application Priority Data

Apr. 30, 2014   (KR) ..................... 10-2014-0052536
May 9, 2014    (WO) ................ PCT/KR2014/004194

(51) Int. Cl.
| | |
|---|---|
| C07K 7/08 | (2006.01) |
| A01N 1/02 | (2006.01) |
| A61K 38/00 | (2006.01) |
| C07K 14/47 | (2006.01) |
| C12N 9/12 | (2006.01) |
| C07K 7/06 | (2006.01) |

(52) U.S. Cl.
CPC .............. *C07K 7/08* (2013.01); *A01N 1/021* (2013.01); *C07K 7/06* (2013.01); *C07K 14/47* (2013.01); *C12N 9/1276* (2013.01); *C12Y 207/07049* (2013.01); *A61K 38/00* (2013.01)

(58) Field of Classification Search
CPC ........ A61K 38/00; C07K 7/08; A01N 1/0215; A01N 1/0221; A01N 1/0226
See application file for complete search history.

(56) References Cited

U.S. PATENT DOCUMENTS

| | | |
|---|---|---|
| 6,967,211 B2 | 11/2005 | Inoue |
| 7,030,211 B1 | 4/2006 | Gaudernack et al. |
| 7,786,084 B2 | 8/2010 | Benner et al. |
| 7,794,723 B2 | 9/2010 | Gaudernack et al. |
| 8,828,403 B2 | 9/2014 | Filaci et al. |
| 8,933,197 B2 | 1/2015 | Bogin et al. |
| 9,023,987 B2 | 5/2015 | Chung et al. |
| 9,540,419 B2 | 1/2017 | Kim et al. |
| 9,572,858 B2 | 2/2017 | Kim et al. |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1 | 5/2006 | Gaudernack et al. |
| 2007/0190561 A1 | 8/2007 | Morin et al. |
| 2008/0025986 A1 | 1/2008 | Ozes et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0065124 A1 | 3/2012 | Morishita et al. |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim |
| 2015/0307859 A1 | 10/2015 | Kim |

(Continued)

FOREIGN PATENT DOCUMENTS

| | | |
|---|---|---|
| EP | 1020190 A3 | 10/2000 |
| EP | 1093381 B2 | 7/2009 |

(Continued)

OTHER PUBLICATIONS

Altschul, S.F., et al., "Basic Local Alignment Search Tool," Journal of Molecular Biology 215(3):403-410, Elsevier, England (1990).
Beer, T.M., et al., "Phase II Study of Weekly Docetaxel in Symptomatic Androgen-independent Prostate Cancer," Annals of Oncology 12(9):1273-1279, Oxford University Press, England (2001).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).

(Continued)

*Primary Examiner* — James H Alstrum-Acevedo
*Assistant Examiner* — Kaipeen E Yang
(74) *Attorney, Agent, or Firm* — Sterne, Kessler, Goldstein & Fox P.L.L.C.

(57) ABSTRACT

Disclosed are: a composition for organ, tissue or cell transplantation, containing, as an active ingredient, a peptide comprising the amino acid sequence of SEQ ID NO: 1, a peptide having at least 80% sequence homology with the amino acid sequence, or a peptide which is a fragment thereof; a kit comprising the composition; or a method using the composition. By using the composition, the kit, or the method, the viability and/or function of an organ, tissue, or cell after transplantation are strengthened and an organ, tissue or cell isolated from a living body is preserved temporarily without damage.

14 Claims, 16 Drawing Sheets

Specification includes a Sequence Listing.

(56) References Cited

U.S. PATENT DOCUMENTS

| | | |
|---|---|---|
| 2015/0343095 A1 | 12/2015 | Kim |
| 2015/0353903 A1 | 12/2015 | Kim |
| 2016/0002613 A1 | 1/2016 | Kim |
| 2016/0008438 A1 | 1/2016 | Kim |
| 2016/0082089 A1 | 3/2016 | Kim |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim |
| 2016/0296604 A1 | 10/2016 | Kim |
| 2016/0375091 A1 | 12/2016 | Kim |
| 2017/0028035 A1 | 2/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 12/2017 | Kim |

FOREIGN PATENT DOCUMENTS

| | | |
|---|---|---|
| EP | 1817337 B1 | 1/2011 |
| JP | 2002522373 A | 7/2002 |
| JP | 2010252810 A | 11/2010 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060065588 A | 6/2006 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130996 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| WO | WO-0002581 A1 | 1/2000 |
| WO | WO-2010003520 A2 | 1/2010 |
| WO | WO-2010012850 A1 | 2/2010 |
| WO | WO-2010128807 A2 | 11/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO-2014046478 A1 | 3/2014 |
| WO | WO-2014046490 A1 | 3/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2016105086 A1 | 6/2016 |
| WO | WO-2016137162 A1 | 9/2016 |
| WO | WO-2017078440 A1 | 5/2017 |

OTHER PUBLICATIONS

Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).

Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).

Brandenburg, K., et al., "Peptide-based Treatment of Sepsis," Applied Microbiology and Biotechnology 90(3):799-808, Springer International, Germany (2011).

Bruns, A.F., et al., "A Heat-shock Protein Axis Regulates VEGFR2 Proteolysis, Blood Vessel Development and Repair," PloS One 7(11):e48539, Public Library of Science, United States (2012).

Brunsvig, P.F., et al., "Telomerase Peptide Vaccination in NSCLC: A Phase II Trial in Stage III Patients Vaccinated after Chemoradiotherapy and An 8-year Update on a Phase I/II Trial," Clinical Cancer Research 17(21):6847-6857, The Association, United States (2011).

Calderwood, S.K., et al., "Heat Shock Proteins in Cancer: Chaperones of Tumorigenesis," Trends in Biochemical Sciences 31(3):164-172, Elsevier Trends Journals, England (2006).

Cho, Y.J., "GemVax & Kael (082270)," Hana Daetoo Securities, Company Report, Sep. 10, 2012,9 pages.

Choi, S.G., "Recent Advances in Cancer Cachexia," Journal of Korean Oncology Nursing 11(1):20-25 (2011).

Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).

Dementia from Merck Manual, accessed on Jul. 29, 2009, pp. 1-17.

Dempsey, N.C., et al., "Differential Heat Shock Protein Localization in Chronic Lymphocytic Leukemia," Journal of Leukocyte Biology 87(3):467-476, Society for Leukocyte Biology, United States (2010).

Dinarello, C.A., "Interleukin-1 in the Pathogenesis and Treatment of Inflammatory Diseases," Blood117(14):3720-3732, American Society of Hematology, United States (2011).

Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).

Engineer, D.R. and Garcia, J.M., "Leptin in Anorexia and Cachexia Syndrome," International Journal of Peptides 2012:Article ID 287457, Hindawi Publishing Corporation, United States (2012).

Eustace, B.K. and Jay, D.G., "Extracellular Roles for the Molecular Chaperone, Hsp90," Cell Cycle 3(9):1098-1100, Taylor & Francis, United States (2004).

Eustace, B.K. et al., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).

Evans, C.G., et al., "Heat Shock Protein 70 (Hsp70) as an Emerging Drug Target," Journal of Medicinal Chemistry 53(12):4585-4602, American Chemical Society, United States (2010).

Ferrarini, M., et al., "Unusual Expression and Localization of Heat-shock Proteins in Human Tumor Cells," International Journal of Cancer51(4):613-619, Wiley-Liss, United States (1992).

Fire, A., et al., "Potent and Specific Genetic Interference by Double-stranded RNA in Caenorhabditis Elegans," Nature 391(6669):806-811, Nature Publishing Group, England (1998).

Fittipaldi, A., et al., "Cell Membrane Lipid Rafts Mediate Caveolar Endocytosis of HIV-1 Tat Fusion Proteins," Journal of Biological

(56) References Cited

OTHER PUBLICATIONS

Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
Garcia-Carbonero, R., et al., "Inhibition of HSP90 Molecular Chaperones: Moving Into the Clinic," The Lancet Oncology 14(9):e358-e369, Lancet Publishing Group, England (2013).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Heitz, F., et al., "Twenty Years of Cell-Penetrating Peptides: From Molecular Mechanisms to Therapeutics," British Journal of Pharmacology 157(2):195-206, Wiley, England (2009).
Heldin, C.H., et al., "TGF-Beta Signalling from Cell Membrane to Nucleus through SMAD Proteins," Nature 390(6659):465-471, Nature Publishing Group, England (1997).
Henry, J.Y., et al., "Lenalidomide Enhances the Anti-prostate Cancer Activity of Docetaxel in vitro and in vivo," The Prostate 72(8):856-867, Wiley-Liss, United States (2012).
Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor and Francis, United States (2012).
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Preliminary Report on Patentability for International Application No. PCT/KR2014/011280, The International Bureau of WIPO, Geneva, Switzerland, dated May 24, 2016, 15 pages.
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014, 14 pages.
International Preliminary Report on Patentability for International Application No. PCT/KR2013/004176, The International Bureau of WIPO, Switzerland, dated Nov. 11, 2014, 14 pages.
International Preliminary Report on Patentability for International Application No. PCT/KR2013/006218, The International Bureau of WIPO, Switzerland, dated Jan. 13, 2015, 27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/KR2014/011280, Korean Intellectual Property Office, Republic of Korea, dated Feb. 11, 2015, 12 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2014/004752, Korean Intellectual Property Office, Republic of Korea, dated Jan. 16, 2015, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Application No. PCT/KR2015/003642, Korean Intellectual Property Office, Republic of Korea, dated Jul. 3, 2015, 8 pages.
International Search Report for International Patent Application No. PCT/KR2013/004156, Korean Intellectual Property Office, Republic of Korea, dated Aug. 14, 2013, 10 pages.
International Search Report for International Application No. PCT/KR2014/012502, Korean Intellectual Property Office, Republic of Korea, dated Mar. 11, 2015, 10 pages.
International Search Report for International Application No. PCT/KR2013/008459, Korean Intellectual Property Office, Republic of Korea, dated Dec. 23, 2013, 8 pages.
International Preliminary Report on Patentability for International Application No. PCT/KR2014/012502, The International Bureau of WIPO, Geneva, Switzerland, dated Jun. 21, 2016, 22 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jemal, A., et al., "Cancer Statistics, 2008," CA: A Cancer Journal for Clinicians 58(2):71-96, Wiley, United States (2008).
Kern, K.A. and Norton, J.A., "Cancer Cachexia," Journal of Parenteral and Enteral Nutrition 12(3):286-298, Sage Publications, United States (1988).
Kim, B.K, et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).

(56) References Cited

OTHER PUBLICATIONS

Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).

Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).

Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).

Kyte, J.A., "Cancer Vaccination with Telomerase Peptide GV1001," Expert Opinion on Investigational Drugs 18(5):687-694, Taylor & Francis, England (2009).

Lahdevirta, J., et al., "Elevated Levels of Circulating Cachectin/tumor Necrosis Factor in Patients with Acquired Immunodeficiency Syndrome," American Journal of Medicine 85(3):289-291, Excerpts Medica, United States (1988).

Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).

Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).

Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).

Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).

Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).

Massague, J., "Tgf-Beta Signal Transduction," Annual Review of Biochemistry 67:753-791, Annual Reviews, United States (1998).

Mattson, M.P., "Pathways Towards and Away From Alzheimer's Disease," Nature 430(7000):631-639, Nature Publishing Group, England (2004).

McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).

Modica-Napolitano, J.S. and Singh, K.K., "Mitochondria as Targets for Detection and Treatment of Cancer," Expert Reviews in Molecular Medicine 4(9):1-19, Cambridge University Press, England (2002).

Morano, K.A., "New Tricks for an Old Dog: the Evolving World of Hsp70," Annals of the New York Academy of Sciences 1113:1-14, Blackwell, United States (2007).

Murphy, M.E., "The Hsp70 Family and Cancer," Carcinogenesis 34(6):1181-1188, Irl Press, England (2013).

Myers, L.K., et al., "Collagen-Induced Arthritis, an Animal Model of Autoimmunity," Life Sciences 61(19):1861-1878, Elsevier, Netherlands (1997).

Ganji, P.N., et al., "Antiangiogenic Effects of Ganetespib in Colorectal Cancer Mediated Through Inhibition of HIF-1α and STAT-3," Angiogenesis 16(4):903-917, Springer, Germany (2013).

National Horizon Scanning Centre News on Emerging Technologies in Healthcare, GV1001 for Advanced and/or Metastatic Pancreatic Cancer, Published Apr. 2008.

NCBI, Reference Sequence: XP_003776612.1 (Jul. 17, 2012).

Novina, C.D. and Sharp, P.A., "The RNAi Revolution," Nature 430(6996):161-164, Nature Publishing Group, England (2004).

Oh, H., et al., "Telomerase Reverse Transcriptase Promotes Cardiac Muscle Cell Proliferation, Hypertrophy, and Survival," Proceedings of the National Academy of Sciences USA 98(18): 10308-10313, National Academy of Sciences, United States (2001).

Pearson, W.R. and Lipman, D.J., "Improved Tools for Biological Sequence Comparison," Proceedings of the National Academy of Sciences USA 85(8):2444-2448, National Academy of Sciences, United States (1988).

Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).

Pfosser, A., et al., "Liposomal HSP90 Cdna Induces Neovascularization via Nitric Oxide in Chronic Ischemia," Cardiovascular Research 65(3):728-736, Oxford Journals, England (2005).

Powers, M.V., et al., "Targeting HSP70: the Second Potentially Druggable Heat Shock Protein and Molecular Chaperone?," Cell Cycle 9(8):1542-1550, Taylor & Francis, United States (2010).

Rana, T.M., "Illuminating the Silence: Understanding the Structure and Function of Small RNAs," Nature Reviews. Molecular Cell Biology 8(1):23-36, Nature Publishing Group, England (2007).

Rheumatoid Arthritis from Merck Manual, accessed on Apr. 21, 2016, pp. 1-18.

Roubenoff, R., et al., "Adjuvant Arthritis as a Model of Inflammatory Cachexia," Arthritis and Rheumatism 40(3):534-539, Wiley-Blackwell, United States (1997).

Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).

Schenk, D, et al., "Immunization with Amyloid-beta Attenuates Alzheimer-disease-like Pathology in the PDAPP Mouse," Nature 400(6740):173-177, Nature Publishing Group, England (1999).

Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).

Seo, J.S., et al., "T Cell Lymphoma in Transgenic Mice Expressing the Human Hsp70 Gene," Biochemical and Biophysical Research Communications 218(2):582-587, Elsevier, United States (1996).

Shay, J.W., and Wright, W.E., "Telomerase Therapeutics for Cancer: Challenges and New Directions," Nature Reviews. Drug Discovery 5(7):577-584, Nature Publishing Group, England (2006).

Smith, D.B. and Johnson, K.S., "Single-step Purification of Polypeptides Expressed in *Escherichia Coli* as Fusions with Glutathione S-transferase," Gene 67(1):31-40, Elsevier, Netherlands (1988).

Smith, T.F. and Waterman, M.S., "Comparison of Biosequences," Advances in Applied Mathematics 2(4):482-489, Academic Press, Inc., United States (1981).

Song, J., et al., "Characterization and Fate of Telomerase-Expressing Epithelia during Kidney Repair," Journal of the American Society of Nephrology 22(12):2256-2265, American Society of Nephrology, United States (2011).

Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.

Stevenson, C.L., "Advances in Peptide Pharmaceuticals," Current Pharmaceutical Biotechnology 10(1):122-137, Bentham Science Publishers, United Arab Emirates (2009).

Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).

(56) References Cited

OTHER PUBLICATIONS

Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "CLUSTAL W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).
Tisdale, M.J., "Mechanisms of Cancer Cachexia," Physiological Reviews 89(2):381-410, American Physiological Society, United States (2009).
Tomari Y. and Zamore, P.D., "Perspective: Machines for RNAi," Genes and Development 19(5):517-529, Cold Spring Harbor Laboratory Press, United States (2005).
Uehara, Y., "Natural Product Origins of Hsp90 Inhibitors," Current Cancer Drug Targets 3(5):325-330, Bentham Science Publishers, Netherlands (2003).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Vennela, B., et al., "Current and Future Strategies for Therapy of Pancreatic Cancer," International Journal of Research in Pharmacy and Medicine 2(3):728-740 (2012).
Volloch, V.Z. and Sherman, M.Y., "Oncogenic Potential of Hsp72," Oncogene 18(24):3648-3651, Nature Publishing Group, England (1999).
Walsmith, J. and Roubenoff, R., "Cachexia in Rheumatoid Arthritis," International Journal of Cardiology 85(1):89-99, Elsevier, Netherlands (2002).
Wang, W., et al., "Alleviating the lschemia-Reperfusion Injury of Donor Liver by Transfection of Exogenous hTERT Genes," Transplantation Proceedings 41(5):1499-1503, Elsevier Science, United States (2009).
Written Opinion for International Application No. PCT/KR2014/011280, Korean Intellectual Property Office, Republic of Korea, dated Feb. 11, 2015, 14 pages.
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2014/004752, Korean Intellectual Property Office, Republic of Korea, dated Jan. 16, 2015, 21 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2015/003642, Korean Intellectual Property Office, Republic of Korea, dated Jul. 3, 2015, 16 pages.
Written Opinion for International Application No. PCT/KR2013/008459, Korean Intellectual Property Office, Republic of Korea, dated Dec. 23, 2013, 9 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Written Opinion for International Application No. PCT/KR2014/012502, Korean Intellectual Property Office, Republic of Korea, dated Mar. 11, 2015, 20 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Yeh, C.H., et al., "Clinical Correlation of Circulating Heat Shock Protein 70 in Acute Leukemia," Leukemia Research 34(5):605-609, Pergamon Press, England (2010).
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).
Zhou, J., et al., "PI3K/Akt Is Required for Heat Shock Proteins to Protect Hypoxia-inducible Factor 1alpha From pVHL-independent Degradation," The Journal of Biological Chemistry 279(14):13506-13513, American Society for Biochemistry and Molecular Biology, United States (2004).
Co-pending U.S. Appl. No. 15/303,370, inventors Kim, Sang Jae, filed Oct. 11, 2016 (Not Yet Published).
Co-pending U.S. Appl. No. 15/307,632, inventors Kim, Sang Jae, filed Oct. 28, 2016 (Not Yet Published).
Co-pending U.S. Appl. No. 15/346,870, inventors Kim, Sang Jae, filed Nov. 9, 2016 (Not Yet Published).
Eisenegger, C., et al., "The Role of Testosterone in Social Interaction," Trends in Cognitive Sciences 15(6):263-271, Elsevier Science, England (2011).
"Seoul National University Bundang Hospital excited because of '000'," Clinical trials of Dream Anticancer Drug without side effects with Kael & GemVax, 4 pages, Apr. 22, 2013.
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).
Guo, R.F., et al., "Regulatory Effects of Eotaxin on Acute Lung Inflammatory Injury," Journal of Immunology 166(8):5208-5218, American Association of Immunologists, United States (2001).
International Preliminary Report on Patentability for International Application No. PCT/KR2014/010035, Korean Intellectual Property Office, Republic of Korea, dated Apr. 26, 2016, 13 pages.
Morishita, M., and Peppas, N.A., "Is the Oral Route Possible for Peptide and Protein Drug Delivery?," Drug Discovery Today 11(19-20):905-910, Elsevier Science Ltd., England (2006).
National Institute of Diabetes and Digestive and Kidney Diseases, "Prostate Enlargement: Benign Prostatic Hyperplasia," Updated Sep. 2014, 14 pages.
Shaw, V.E., et al., "Current Status of GV1001 and Other Telomerase Vaccination Strategies in the Treatment of Cancer," Expert Review of Vaccines 9(9):1007-1016, Taylor & Francis, England (2010).
Sasada, A, et al. "A case of elderly patient with lung cancer efficiently treated with Dendritic Cell Immunotherapy," The 20th International Congress of Personalized Medicine, Conference Program and Abstracts, Personalized Medicine Universe (Japanese edition) 4(Supplement 1): 2 pages, May 24, 2015.
Kawasaki, H, et al. "Detection and evaluation of activation of various cancer antigenic peptide-specific CTLs in mature dendritic

(56) References Cited

OTHER PUBLICATIONS cells used for dendritic cell therapy," The 21st International Congress of Personalized Medicine, Conference Program and Abstracts, Personalized Medicine Universe (Japanese edition) 4(Supplement 2): 5 pages, Oct. 17, 2015.

Written Opinion for International Application No. PCT/KR2014/010035, Korean Intellectual Property Office, Republic of Korea, dated Feb. 2, 2015, 11 pages.

Co-pending U.S. Appl. No. 15/479,746, inventors Kim, S.J., et al., filed Apr. 5, 2017 (Not Published).

ClinicalTrials.gov, "Gemcitabine, Capecitabine, and Telomerase Peptide Vaccine GV1001 in Treating Patients With Locally Advanced and Metastatic Pancreatic Cancer," Identifier NCT00425360, accessed at https://clinicaltrials.gov/archive/NCT00425360/2007_01_22, last accessed on Apr. 7, 2017, 4 pages.

ClinicalTrials.gov, "Adjuvant Leuprolide with or without Docetaxel in High Risk Prostate Cancer After Radial Prostatectomy," Identifier NCT00283062, accessed at https://clinicaltrials.gov/ct2/show/study/NCT00283062, last accessed on May 12, 2017, 7 pages.

Kyte, J.A., et al., "Telomerase Peptide Vaccination Combined with Temozolomide: A Clinical Trial in Stage IV Melanoma Patients," Clinical Cancer Research 17(13):4568-4580, The American Association of Cancer Research, United States (2011).

Mandal, A., "Types of Fibrosis," news-medical.net, accessed at http://www.news-medical.net/health/Types-of-Fibrosis.aspx, last accessed on Jul. 3, 2014, 3 pages.

Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet. Oncology 15(8):829-840, Lancet Pub. Group, England (Jul. 2014).

National Center for Biotechnology Information, "Hormones," MeSH Database, Bethesda, accessed at http://www.ncbi.nlm.nih.gov/mesh/68006728, accessed on May 8, 2017, 3 pages.

Nawroth, I., et al., "Intraperitoneal Administration of Chitosan/DsiRNA Nanoparticles Targeting TNFα Prevents Radiation-induced Fibrosis," Radiotherapy and Oncology 97(1):143-148, Elsevier Ireland Ltd., Ireland (2010).

Rosenbloom, J., et al., "Strategies for Anti-fibrotic Therapies," Biochimica et Biophysica Acta 1832(7):1088-1103, Elsevier B.V., Netherlands (2013).

Tisdale, M.J., "Catabolic Mediators of Cancer Cachexia," Current Opinion in Supportive and Palliative Care, 2(4):256-261, Lippincott Williams & Wilkins, United States (2008).

Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).

International Preliminary Report on Patentability and Written Opinion for International Application No. PCT/KR2015/014099, The International Bureau of WIPO, dated Jun. 27, 2017, 16 pages.

International Search Report for International Application No. PCT/KR2015/014099, Korean Intellectual Property Office, Republic of Korea, dated May 4, 2016, 8 pages.

International Search Report for International Application No. PCT/KR2016/001646, Korean Intellectual Property Office, Republic of Korea, dated May 4, 2016, 8 pages.

De Araujo, J.G., et al., "The Potential Use of Melatonin for Preventing Cisplatin Ototoxicity: An Insight for a Clinical Approach," Advances in Otolaryngology vol. 2014, Article ID 185617, Hindawi Publishing Corporation, 8 pages (2014).

Kim, B-H., "Presbycusis: Review for its Environmental Risk Factors," Korean J Otorhinolaryngol—Head Neck Surgery 49(10):962-967, Korean Society of Otolaryngology—Head and Neck Surgery, Korea (2006).

Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (2015).

Rovve-Rendleman, C. and Glickman, R.D., "Possible therapy for age-related macular degeneration using human telomerase," Brain Research Bulletin 62(6):549-553, Elsevier Science Inc., United States (2004).

Co-pending U.S. Appl. No. 15/539,396, inventor Kim, S.J., et al., I.A. filed Dec. 22, 2015 (Not Published).

Auerbach, R., et al., "Angiogenesis Assays: Problems and Pitfalls," Cancer Metastasis Reviews 19(1-2):167-172, Kluwer Academic, Netherlands (2000).

Berendsen, H.J., "A Glimpse of the Holy Grail?," Science 282(5389):642-643, American Association for the Advancement of Science, United States (1998).

Co-pending U.S. Appl. No. 15/772,928, inventors Kim, S.J., et al., filed Nov. 3, 2016 (Not Published).

Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.

Du, C., et al., "Conformational and Topological Requirements of Cell-permeable Peptide Function," The Journal of Peptide Research 51(3):235-243, Munksgaard, Denmark (1998).

Fauce, S.R., et al., "Telomerase-Based Pharmacologic Enhancement of Antiviral function of Human CD8+ T Lymphocytes, "Immunology 181(10):7400-7406, American Association of Immunologists, United States (Nov. 2008).

Fontanes, V., et al., "A cell permeable peptide inhibits Hepatitis C Virus Replication by Sequestering IRES Transacting Factors," Virology 394(1):82-90, Academic Press, United States (Nov. 2009).

Fried, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.

International Search Report and Written Opinion for International Application No. PCT/KR2016/012613, Korean Intellectual Property Office, Republic of Korea, dated Feb. 2, 2017, 14 pages.

International Search Report for Application No. PCT/KR2016/007192, dated Sep. 12, 2016, 12 pages.

Jain, R.K., "Barriers to Drug Delivery in Solid Tumors," Scientific American 271(1):58-65, Scientific American, Inc., United States (Jul. 1994).

Kalnins, A., et al., "Sequence of the Lacz Gene of *Escherichia Coli*," The EMBO Journal 2(4):593-597, Wiley Blackwell, England (1983).

Kim, H., et al., "Inhibition of HIV-1 Reactivation by a Telomerase-Derived Peptide in a HSP90-Dependent Manner," Scientific Reports 6: 28896, Nature Publishing Group, England (Jul. 2016).

Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).

Lee, S.A., et al., "A Telomerase-Derived Peptide Regulates Reactive Oxygen Species and Hepatitis C Virus RNA Replication in HCV-Infected Cells Via Heat Shock Protein 90," Biochemical and Biophysical Research Communications 471(1):156-162, Elsevier, United States (Feb. 2016).

Leem G., et al., Immunotherapy in Pancreatic Cancer; the Road Less Traveled Immunol Disord Immunotherapy, Jun. 26, 2016 (Jun. 26, 2016), p. 1000106, XP055328627, Retrieved from the Internet: (URL:http://www.omicsgroup.orgjjournalsjimmunotherapy-in-pancreatic-cancer-the-road-less-traveled-IDIT-1000104.pdf).

Merck Manual: Respiratory Diseases, Medical Topics, accessed on Nov. 2, 2017, pp. 1-4.

Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.

Middleton, G.W., "A Phase III Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL:http://meetinglibrary.asco.orgjcontent/82894?media=vm).

(56) References Cited

OTHER PUBLICATIONS

Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013)-(Jun. 4, 2013), XP055328310.
Middleton, G.W., et al., Poster: Predictive Cytokine Biomarkers for Survival in Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun. 3, 2014), pp. 1-1. XP055328448. Retrieved from the Internet: (URL:http://media4.asco.org/144/8599/93976/93976_poster_pvhr.jpg).
Neoptolemos J.P., et al., "Predictive 1-20 Cytokine Biomarkers for Survival in Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial," 2014 ASCO Annual Meeting, May 30, 2014 (May 30, 2014)-Jun. 3, 2014 (Jun. 3, 2014), pp. 1-3.
Ngo. et al., "Computational Complexity, Protein Structure Prediction, and the Levinthal Paradox," in The Protein Folding Problem and Tertiary Structure Prediction, Merz, Jr., K.M., and Le Grand, S.M., eds., pp. 491-494, Birkhauser Boston, United States (1994).
Ortega, V.E., "Asthma," Merck manual, accessed at http://www.merckmanuals.com/professional/pulmonary-disorders/asthma-and-related-disorders/asthma, accessed on Nov. 2, 2017, pp. 1-19.
Albini, A., et al., "Cancer Prevention by Targeting Angiogenesis," Nature reviews Clinical oncology 9(9):498-509, Nature Pub Group (2012).
Extended European Search Report for Application No. EP14808179, dated May 24, 2017, 24 pages.
O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).
Priya, S.G., et al., "Skin Tissue Engineering for Tissue Repair and Regeneration," Tissue Engineering. Part B, Reviews 14(1):105-118, Mary Ann Liebert, Inc., United States (2008).
Supplemental European Search Report for Application No. EP14808179, dated Jan. 10, 2017, 13 pages.
Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Apr 2011).
Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.
Rudinger, J., "Characteristics of the Amino Acids as Components of a Peptide Hormone Sequence," in Peptide Hormones, Parsons, J.A., ed., University Park Press, United States (1976).
Schwarze, S.R., et al., "In Vivo Protein Transduction: Delivery of a Biologically Active Protein Into the Mouse," Science 285(5433):1569-1572, American Association for the Advancement of Science, United States (1999).
Sigma Genosys, "Designing Custom Peptides," accessed at http://www.sigma-genosys.com/peptide_design.asp, Accessed on Dec. 16, 2004, 2 pages.
International Preliminary Report on Patentability and Written Opinion for International Application No. PCT/KR2016/001646, Korean Intellectual Property Office, Republic of Korea, dated May 20, 2016, 13 pages.
Voet, D. and Voet, J.G., "Abnormal Hemoglobins," in Biochemistry, 2nd Edition, Chapter 9, pp. 235-241, John Wiley & Sons, Inc., United States (1995).
Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).
Written opinion for Application No. PCT/KR2016/007192, dated Sep. 12, 2016, 16 pages.

Normal Saline
 Perfadex
 Perfadex + PEP1 5mg
 Perfadex + PEP1 50mg

SEQUENCE LISTING

<160> NUMBER OF SEQ ID NOS: 2

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro

```
            305                 310                 315                 320
Cys Pro Pro Val Ala Glu Thr Lys His Phe Leu Tyr Ser Ser Gly
                325                 330                 335
Asp Lys Glu Gln Leu Arg Pro Ser Phe Leu Ser Ser Leu Arg Pro
                340                 345                 350
Ser Leu Thr Gly Ala Arg Arg Leu Val Glu Thr Ile Phe Leu Gly Ser
                355                 360                 365
Arg Pro Trp Met Pro Gly Thr Pro Arg Arg Leu Pro Arg Leu Pro Gln
        370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
                420                 425                 430
Gly Ser Val Ala Ala Pro Glu Glu Asp Thr Asp Pro Arg Arg Leu
                435                 440                 445
Val Gln Leu Leu Arg Gln His Ser Ser Pro Trp Gln Val Tyr Gly Phe
        450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
                500                 505                 510
Ser Val Arg Asp Cys Ala Trp Leu Arg Arg Ser Pro Gly Val Gly Cys
        515                 520                 525
Val Pro Ala Ala Glu His Arg Leu Arg Glu Glu Ile Leu Ala Lys Phe
        530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
                580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
        610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
                660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro
        690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
```

-continued

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

COMPOSITION FOR ORGAN, TISSUE, OR CELL TRANSPLANTATION, KIT, AND TRANSPLANTATION METHOD

TECHNICAL FIELD

The present invention relates to a composition for organ, tissue or cell transplantation; a kit for organ, tissue or cell transplantation; or a method for organ, tissue or cell transplantation.

BACKGROUND ART

Organ transplantation is the transfer of tissue or an organ from an original site to another to replace damaged tissue or organ. The organ transplantation may have various problems, one of which is ischemic tissue injury due to ischemia-reperfusion (IR). The ischemic tissue injury caused by IR occurring in the organ transplantation results in delaying the recovery of renal function after the organ transplantation, which causes an inflammatory tissue reaction often serving as a prognostic factor that is bad for long-term maintenance of the function of the transplanted organ. Early IR injury incidentally occurring in the organ transplantation may lead to subsequent deterioration of the organ function and transplantation failure.

Particularly, lung transplantation is known as the sole therapeutic option for terminal lung diseases, and it is expected that patients' demands for lung transplantation will constantly increase. However, despite steady medical advancement, lung transplantation survivability is still not higher than other organs. The most frequently occurring problem at the early stage after a lung transplant is graft dysfunction, one cause of which is an IR injury.

Meanwhile, a flap is a piece of skin or tissue with a pedicle or tissue similar thereto, which is transferred from one site to another site of the body, the transferred tissue capable of surviving in the pedicle or tissue similar thereto. Flap surgery is a surgery technique that is most widely used in plastic and reconstructive surgeries for soft tissue defects or chronic wounds, which cannot be dealt with through skin transplantation, and useful for reconstructing an appearance and lost function, and particularly, the flap surgery can rapidly restore the defects or wounds by a primary reconstruction through transplantation of a combination of various types of tissue such as bones, tendons, muscles, and nerves. In the flap surgery, flap survivability is closely related to an IR injury treatment. Therefore, it is expected that a method for stably enhancing the flap survivability through the IR injury treatment will be very useful.

Also, cell transplantation, similarly to organ or tissue transplantation, is carried out to treat a disease, and as a representative example, transplantation of cells in the islets of Langerhans for improving type 1 diabetes may be used. Within the first week of the transplantation of the islets of Langerhans, most of the grafts are lost, which may be because they are exposed to various stress factors such as hypoxia, and to proinflammatory cytokines and free radicals before secondary angiogenesis after the transplantation.

PRIOR ART DOCUMENT

Non-Patent Document

Granger et al. Ann. Rev. Physiol., 57, 311-332, (1995)

DISCLOSURE

Technical Problem

An object of the present invention is directed to promoting survivability and/or functions of organs, tissue and individual cell grafts.

Another object of the present invention is directed to strengthening the survivability and/or function of an organ, tissue or cell graft after transplantation.

Still another object of the present invention is directed to providing a method and/or composition for temporarily storing an organ, tissue or cells without damage.

Technical Solution

In one aspect, the present invention provides a composition for organ, tissue or cell transplantation, which comprises, as an active ingredient, a peptide comprising the amino acid sequence of SEQ ID NO: 1, a peptide having at least 80% sequence homology with the amino acid sequence or a fragment thereof. In the composition, the fragment may be a fragment composed of three or more amino acids.

In one aspect, the composition may be administered to a donor and/or recipient.

In one aspect, the composition may be administered in at least one stage before, during and after transplantation.

In another aspect, the composition may be to store an organ, tissue or cells isolated from a donor.

In one aspect, the composition may comprise the peptide as the active ingredient at a sufficient amount for strengthening the survivability or function of an organ, tissue or cell after being transplanted to a recipient.

In one aspect, the composition may comprise the peptide as the active ingredient at a concentration of 10 to 1000 mg/L with respect to the total volume of the composition.

In one aspect, the composition may comprise the peptide as the active ingredient at a concentration of 50 to 500 mg/L with respect to the total volume of the composition.

In one aspect, the present invention may provide a kit for organ, tissue or cell transplantation, comprising a composition for organ, tissue or cell transplantation; and a protocol including a method for using the composition.

In one aspect, in the kit, the composition may be at least one of a composition administered to a donor before transplantation; a composition administered to a recipient before transplantation; a composition administered to a donor during transplantation; a composition administered to a recipient during transplantation; a composition for storing organ, tissue or cells isolated from a donor; a composition administered to a donor after transplantation; and a composition administered to a recipient after transplantation.

In another aspect, in the kit, the protocol may include doses, administration methods and administration intervals for the respective compositions.

In the kit according to another aspect, the protocol may include the administration of the composition through perfusion of an organ, tissue or cells in a donor's or recipient's body with the organ, tissue or cells present in the body.

In another aspect, the present invention may provide a method for organ, tissue or cell transplantation, which comprises treating an isolated organ, tissue or cells with at least one of the above-described compositions for organ, tissue or cell transplantation, or administering at least one of the above-described compositions for organ, tissue or cell transplantation to a donor and/or recipient for the organ, tissue or cell transplantation.

In another aspect, the method may comprise at least one of administration of the composition to a donor before transplantation; administration of the composition to a recipient before transplantation; administration of the composition to a donor during transplantation; administration of the composition to a recipient during transplantation; storage of an organ, tissue or cells isolated from a donor in the composition; administration of the composition to a recipient after transplantation; and administration of the composition to a donor after transplantation.

In one aspect, the method may comprise administering the composition by perfusing an organ, tissue or cells in a donor's or recipient's body with the organ, tissue or cells present in the body.

In another aspect, the composition may be treated or administered at a single dose of 1 to 10000 mg based on a 60-kg adult.

In another aspect, the composition may be treated or administered at a single dose of 200 to 5000 mg based on a 60-kg adult.

In one aspect, the present invention may provide a use of at least one of the above-described compositions to treat an isolated organ, tissue or cells, or to be administered to a donor and/or recipient of organ, tissue or cell transplantation.

Advantageous Effects

In one aspect, the present invention can promote the survivability and/or functions of organ, tissue, and individual cell grafts.

In another aspect, the present invention can strengthen the survivability and/or function after organ, tissue or cell transplantation.

In still another aspect, the present invention can temporarily store an organ, tissue or cells without damage.

MODES OF THE INVENTION

Figure 1:
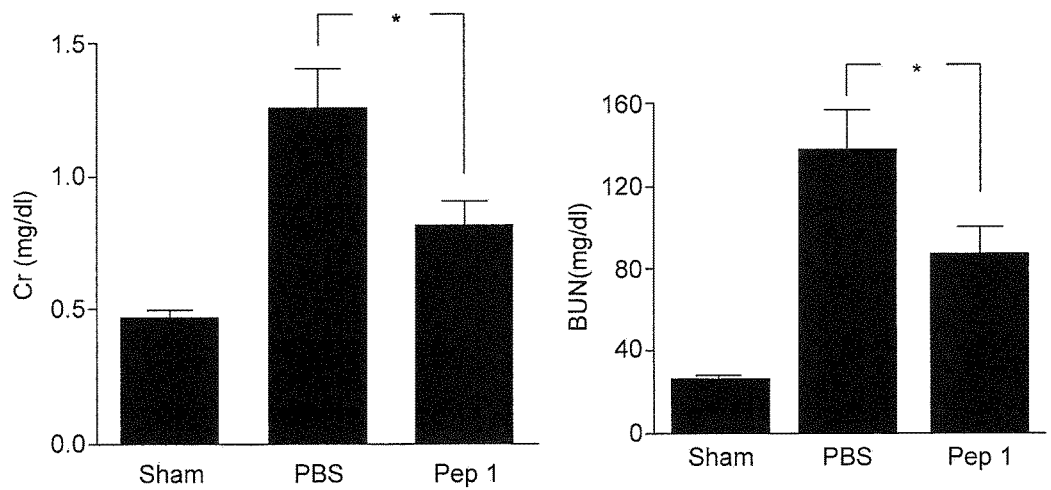
FIG. 1 show graphs showing levels of blood urea nitrogen (BUN) and creatine, which are taken after 24 hours of IR.

The present invention may be modified in various forms and have many examples, and thus will be described in detail based on the examples below. However, these examples are not provided to limit the present invention to specific embodiments, and it should be understood that the present invention can have various examples and applications as described in the claims, and comprises all modifications, equivalents and alternatives within the spirit and technical scope of the present invention. To explain the present invention, if it is determined that a detailed description of related art may obscure the gist of the present invention, the detailed description will be omitted.

Telomere, which is a repetitive genetic material located at each terminus of a chromosome, is known to prevent damage in a corresponding chromosome or coupling to a different chromosome. The telomere is gradually shortened with cell divisions, becoming very short after a certain number of cell divisions, and the cell eventually stops being divided and dies. On the other hand, the elongation of telomeres is known to extend the life span of a cell. As an example, it has been known that, in cancer cells, an enzyme called telomerase is secreted to prevent the shortening of telomeres, resulting in steady proliferation of the cancer cells, without death. In one aspect, the present invention relates to a composition or kit, which is used to treat a donor, recipient, organ, tissue, the cluster of cells and/or each cell in any step of extraction, storage and transplantation of an organ, tissue or cells. The organ, tissue the cluster of cells or each cell may be extracted from a donor, treated with the composition disclosed in the specification, and transplanted into a recipient. In another aspect, in addition to the above-described method, the organ, tissue the cluster of cells or each cell may be treated in a donor's body while present in the body. Selectively, the organ is reperfused with the composition disclosed in the specification, for example, a recipient's blood before, during and/or after a surgery. Also, the composition disclosed the specification may be administered to a donor before or during extraction of an organ, tissue, cluster of cells or each cell.

In one aspect of the present invention, a peptide of SEQ ID NO: 1, a fragment of the peptide of SEQ ID NO: 1 or a peptide having at least 80% sequence homology with the peptide sequence comprises telomerase, specifically, a peptide derived from Homo sapiens telomerase.

The peptide set forth in SEQ ID NO: 1 is shown in Table 1 below. The "name" in Table 1 below is given to distinguish one peptide to another. In one aspect of the present invention, the peptide set forth in SEQ ID NO: 1 represents the whole peptide of Homo sapiens telomerase. In another aspect of the present invention, the peptide comprising the sequence of SEQ ID NO: 1, the fragment of the peptide comprising the sequence of SEQ ID NO: 1 or the peptide having at least 80% sequence homology with the peptide sequence includes a "synthetic peptide" synthesized from a peptide present at a corresponding location of the peptides included in the telomerase. SEQ. ID. NO: 2 denotes the full-length amino acid sequence of the telomerase.

TABLE 1

| SEQ ID NO | Name | Position on telomerase | Sequence | Length |
|---|---|---|---|---|
| 1 | pep1 | [611-626] | EARPALLTSRLRFIPK | 16 aa |
| 2 | | [1-1132] | MPRAPRCRAVRSLLRS HYREVLPLATFVRRLG PQGWRLVQRGDPAAFR ALVAQCLVCVPWDARP PPAAPSFRQVSCLKEL VARVLQRLCERGAKNV LAFGFALLDGARGGPP EAFTTSVRSYLPNTVT DALRGSGAWGLLLRRV GDDVLVHLLARCALFV LVAPSCAYQVCGPPLY QLGAATQARPPPHASG PRRRLGCERAWNHSVR EAGVPLGLPAPGARRR GGSASRSLPLPKRPRR GAAPEPERTPVGQGSW AHPGRTRGPSDRGFCV VSPARPAEEATSLEGA LSGTRHSHPSVGRQHH AGPPSTSRPPRPWDTP CPPVYAETKHFLYSSG DKEQLRPSFLLSSLRP SLTGARRLVETIFLGS RPWMPGTPRRLPRLPQ RYWQMRPLFLELLGNH AQCPYGVLLKTHCPLR AAVTPAAGVCAREKPQ GSVAAPEEEDTDPRRL VQLLRQHSSPWQVYGF VRACLRRLVPPGLWGS RHNERRFLRNTKKFIS LGKHAKLSLQELTWKM SVRDCAWLRRSPGVGC VPAAEHRLREEILAKF LHWLMSVYVVELLRSF FYVTETTFQKNRLFFY RKSVWSKLQSIGIRQH LKRVQLRELSEAEVRQ HREARPALLTSRLRFI PKPDGLRPIVNMDYVV GARTFRRAKRAERLTS RVKALFSVLNYERARR PGLLGASVLGLDDIHR AWRTFVLRVRAQDPPP ELYFVKVDVTGAYDTI PQDRLTEVIASIIKPQ NTYCVRRYAVVQKAAH GHVRKAFKSHVSTLTD LQPYMRQFVAHLQETS PLRDAVVIEQSSSLNE ASSGLFDVFLRFMCHH AVRIRGKSYVQCQGIP QGSILSTLLCSLCYGD MENKLFAGIRRDGLLL RLVDDFLLVTPHLTHA KTFLRTLVRGVPEYGC VVNLRKTVVNFPVEDE ALGGTAFVQMPAHGLF PWCGLLLDTRTLEVQS DYSSYARTSIRASLTF NRGFKAGRNMRRKLFG VLRLKCHSLFLDLQVN SLQTVCTNIYKILLLQ AYRFHACVLQLPFHQQ VWKNPTFFLRVISDTA SLCYSILKAKNAGMSL GAKGAAGPLPSEAVQW LCHQAFLLKLTRHRVT YVPLLGSLRTAQTQLS RKLPGT TLTALEAAA NPALPSDFKTILD | 1132 aa |

The peptide disclosed in the specification may include a peptide having 80% or higher, 85% or higher, 90% or higher, 95% or higher, 96% or higher, 97% or higher, 98% or higher, or 99% or higher sequence homology. Also, the peptide disclosed in the specification may include a peptide having at least one, two, three, four, five, six, or seven different amino acids from the peptide of SEQ ID NO: 1 or a fragment thereof.

In one aspect of the present invention, the amino acid change is one of the properties that change physicochemical characteristics of the peptide. For example, amino acids may be changed to enhance thermal stability, change substrate specificity, and shift an optimal pH of the peptide.

The term "amino acid" used herein not only includes the 22 standard amino acids that are naturally integrated into a peptide, but also includes the D-isomers and transformed amino acids. Therefore, in one aspect of the present invention, the peptide may be a peptide including a D-amino acid. On the other hand, in another aspect of the present invention, the peptide may include a non-standard amino acid, which is subjected to post-translational modification. Examples of the post-translational modification include phosphorylation, glycosylation, acylation (including acetylation, myristorylation, and palmitoylation), alkylation, carboxylation, hydroxylation, glycation, biotinylation, ubiquitinylation, a change in chemical properties (e.g. β-removing deimidation, deamidation), and a structural change (e.g. formation of a disulfide bridge). The post-translational modification also includes changes of amino acids occurring due to chemical reactions during coupling with crosslinkers for formation of a peptide conjugate, for example, a change in an amino acid such as a change in an amino group, a carboxyl group, or a side chain.

The peptide disclosed herein may be a wild-type peptide identified and isolated from a natural source. Meanwhile, the peptide disclosed in the specification may be an artificial variant comprising an amino acid sequence in which one or more amino acids are substituted, deleted, and/or inserted compared with the fragments of the peptide of SEQ. ID. NO: 1. The changing of amino acids in the wild-type polypeptide, as well as the artificial variant, includes substitutions of conservative amino acids, which does not have a significant influence on folding and/or activity of a protein. The conservative substitution may be carried out within the range of the group consisting of basic amino acids (arginine, lysine and histidine), acidic amino acid (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Generally, amino acid substitutions that do not change specific activities are known in the art. The most frequently-occurring exchange takes place between Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, and vice versa. Other examples of the conservative substitution are shown in Table 2 below.

TABLE 2

| Original amino acid | Exemplary residue substitution | Preferred residue substitution |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |
| Ser (S) | thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

In terms of biological properties of the peptide, a substantial modification is performed by selecting a substitution part which has a considerably different effect in (a) maintaining the backbone structure, for example, a sheet- or helix-like three-dimensional structure, of the polypeptide in the substituted region, (b) maintaining charge or hydrophobicity of the molecule at a target site, or (c) maintaining the bulk of a side chain. Natural residues are classified into the following groups, based on general properties of the side chain:
(1) Hydrophobic: norleucine, met, ala, val, leu, ile;
(2) Neutral hydrophilic: cys, ser, thr;
(3) Acidic: asp, glu;
(4) Basic: asn, gin, his, lys, arg;
(5) Residues affecting chain conformation: gly, pro; and
(6) Aromatic: trp, tyr, phe.

Non-conservative substitutions may be performed by exchanging a member of one of the groups to that of another group. Any cysteine residue, which is not associated with maintaining the proper three-dimensional structure of the peptide, may typically be substituted into serine, thus increasing the oxidative stability of the molecule and preventing improper crosslinks, and, conversely, enhanced stability can be achieved by adding cysteine bond(s) to the peptide.

A different type of amino acid variant of the peptide is made by changing a glycosylation pattern of an antibody. The term "change" used herein refers to deletion of one or more carbohydrate residues that are found on the peptide and/or addition of one or more glycosylation sites which do not exist in the peptide.

Glycosylation in peptides are typically N- or O-linked glycosylation. The term "N linked glycosylation" used herein refers to attachment of carbohydrate residues to side chains of asparagine residues. As tripeptide sequences, asparagine-X-serine and asparagine-X-threonine (where the X is any amino acid, excluding proline) are recognition sequences for enzymatically attaching a carbohydrate residue to a side chain of an asparagine. Therefore, when one of these tripeptide sequences is present in a polypeptide, a potential glycosylation site is created. The "O-linked glycosylation" used herein refers to the attachment of one of the saccharides, for example, N-acetylgalactosamine, galactose, or xylose, to hydroxyamino acids and, most typically, to serine or threonine, but 5-hydroxyproline or 5-hydroxylysine may also be used.

Addition of a glycosylation site to the peptide is conveniently performed by changing the amino acid sequence to contain the tripeptide sequence described above (for an N-linked glycosylation site). Such a change may be made by addition of one or more serine or threonine residues to the first antibody sequence or substitution of the first antibody sequence with one or more serine or threonine residues (for an O-linked glycosylation site).

The term "cells" used herein refers to a random type of animal cells such as animal cells suitable for transplantation. The cells may be generally primary cells obtained from an animal donor, secondary cells from an established cell line or equivalent cells thereof. These cells are transfected in vitro by an expression vector that selectively changes a function of the cells in a certain method. The cells include, not in a limiting manner, for example, cells in the islets of Langerhans, such as cells that are a part of the pancreatic islets of Langerhans, liver cells, fibroblasts, bone marrow cells, myocytes and stem cells, and cells in the central nerve system such as the spinal cord (e.g., nerve cells). Throughout the specification, the "cell(s) in the islets of Langerhans" is a general term used to describe the cluster of cells present in the pancreas, known as the islet, for example, the islets of Langerhans. In the islets of Langerhans, several types of cells, for example, n-cells (insulin production), α-cells (glucagon production), v-cells (somatostatin production), F cells (pancreatic polypeptide production), enterochromaffin cells (serotonin production), PP cells and Dl cells are included. The term "stem cells" is a known term in the art referring to cells that have an ability to be indefinitely divided in a culture medium to become differentiated cells. The stem cells include, for example, totipotent, pluripotent, multipotent and unipotent stem cells, such as neuronal cells, liver cells, myocytes, and hematopoietic progenitor cells.

The term "organ" used herein is a general term used to describe any anatomical part or member having a specific function in an animal throughout the specification. Also, the organ includes, for example, a part corresponding to the organ such as cohesion tissue obtained from the organ. Such an organ unlimitedly includes the kidney, the liver, the heart, the stomach, the intestine such as a large or small intestine, the pancreas, the skin and the lung. The organ also includes the bone, skeletal muscles, abdominal muscles, limbs, the mesentery, and blood vessels such as an aortic transplant.

The term "transplantation" used herein is a general term used to describe a process of transplanting an organ, tissue, a cluster of cells, or an individual cell into a patient. The term "transplantation" used herein refers to a process of delivering surviving tissue or cells from a donor to a recipient to maintain functional integrity of the tissue or cells transplanted into the recipient.

The "administration during transplantation" used herein refers to administration in the entire process of a transplantation surgery. That is, the administration during transplantation includes the administration right after the extraction of an organ, tissue, or cell from a donor, during the surgery for transplanting the extracted organ, tissue, or cell into a recipient, and right after the transplant.

The "administration before transplantation" used herein includes administration of the composition disclosed in the specification to a donor and/or a recipient several minutes, hours, days, or tens of days before a surgery as a preparation step for a transplantation surgery.

The "administration after transplantation" used herein includes the administration of the composition disclosed in the specification to a recipient several minutes, hours, days, tens of days, hundreds of days after a surgery as a maintenance step of a transplantation surgery.

In the present invention, the "ischemic injury" refers to a fatal injury occurring as a result of interruption of blood circulation and thus reduction of oxygen transfer in an organ requiring blood supply, such as the heart, brain, kidney and lung, leading to a dysfunction of tissue and apoptosis. The cause of such an ischemic injury includes, but is not limited to, a vascular disease, coronary thrombosis, cerebrovascular thrombosis, aneurysm rupture, systemic hemorrhage, a crush injury, sepsis, severe skin burn, vascular ligation surgery (e.g., spinal ischemia during thoracoabdominal aneurysm surgery), cardiopulmonary bypass, organ transplantation, cardiopulmonary collapse (sudden cardiac death), suffocation.

Also, the "ischemic injury" according to the present invention includes an IR injury that can be caused by organ transplantation, other than ischemic injury that can conventionally occur. The IR injury includes cerebrovascular ischemic-reperfusion injury, renal ischemic-reperfusion injury, hepatic ischemic-reperfusion injury, ischemic-reperfusion cardiomyopathy, ischemic-reperfusion skin injury, gastrointestinal ischemic-reperfusion injury, intestinal ischemic-reperfusion injury, gastric ischemic-reperfusion injury, ischemic-reperfusion lung injury, pancreatic ischemic-reperfusion injury, ischemic-reperfusion skeletal muscle injury, ischemic-reperfusion abdominal muscle injury, ischemic-reperfusion limb injury, ischemic-reperfusion colitis, mesenteric ischemic-reperfusion injury, and asymptomatic ischemic-reperfusion injury but is not limited thereto.

The IR injury may frequently occur during organ transplantation surgery. For example, it is known that gradual functional loss and a dysfunction of a transplanted kidney are associated with the IR injury in renal transplantation, and the activation of the innate immune system by the IR tissue injury is one of the important causes.

In one aspect, the present invention provides a transplantation method, which comprises: administering the peptide-containing composition into a transplant donor; obtaining an organ, tissue or cells from the donor; and transplanting the obtained organ, tissue or cells into a recipient. In this method, an amount of the peptide administered into the donor is an amount sufficient for strengthening the survivability or function of an organ, tissue or cell after being transplanted into the recipient. Here, the administration to the donor may be continuously performed during or right before a surgery and in the preparation step before the surgery and/or the maintenance step after the surgery. The donor may be a surviving donor, brain dead donor, or a donor before or after brain death.

In another aspect, the present invention provides a transplantation method, which comprises: obtaining an organ, tissue or cells from a donor; maintaining the obtained organ, tissue or cells in a composition containing the peptide; and transplanting the stored organ, tissue or cells into a recipient. In this method, an amount of the peptide in the composition for storing the organ, tissue or cells is an amount that is sufficient for strengthening the survivability or function of the organ, tissue or cells transplanted into the recipient.

In another aspect, the present invention provides a transplantation method, which comprises: obtaining an organ, tissue or cells from a donor transplanting the obtained organ, tissue or cells into a recipient; and administering the composition containing the peptide into the recipient. In this method, an amount of the peptide administered to the recipient is an amount that is sufficient for strengthening the survivability or function of the organ, tissue or cells after being transplanted into the recipient. Here, the administration to the recipient may be continuously performed during or right after the surgery, and in a maintenance step after the surgery.

In one embodiment, the composition disclosed in the specification may be administered to a recipient within 0 to 20 days, for example, 1, 2, 4, 6, 8, 10, 12, 14, 18, or 20 days, after transplanting an organ, tissue or cells into the recipient. In another embodiment, the composition disclosed in the specification may be administered to a recipient at least once, for example, several times or continuously, from day 21 after transplanting the organ, tissue or cells into the recipient for a long time as long as needed for ensuring the survival of the transplant. The composition disclosed in the specification may be administered to the recipient in a suitable form determined whether rejection of the transplanted organ, tissue or cells is exhibited, for example, chronic or acute rejection.

In one aspect, the composition comprising the peptide may be administered to both of a donor and a recipient. In another aspect, the composition comprising the peptide may be administered to a donor and/or recipient, and during the transplantation, an organ, tissue or cells may be temporarily stored in the composition comprising the peptide.

In one embodiment, the composition disclosed in the specification may be administered by perfusing an organ, tissue or cells in a donor's or recipient's body with the organ, tissue or cells present in the body.

In the method described in the specification, the organ, tissue or cell may be any organ, tissue or cell which may be transplanted. For example, the organ may be the liver, kidney, heart, pancreas, lung, small intestine and/or skin, and tissue or cells thereof.

The donor may be heterologous or homologous to the recipient. Both the donor and recipient may be animals except humans, or humans. Also, the donor may be an animal excluding a human, for example, a pig, or the recipient may be a human. In one embodiment, the tissue or cells may be own tissue or cells of the recipient. In other words, the donor and the recipient may be the same individual.

The composition disclosed in the specification may comprise the peptide as an active ingredient in combination with another active ingredient. For example, the peptide disclosed in the specification may be added to PERFADEX™ (a lightly buffered colloid-based electrolyte preservation solution for rapid cooling, perfusion and storage of organs in connection with transplantation manufacture by XVIVO Perfusion AB), which is commercially available as a lung preservation solution.

In the composition disclosed in the specification, a concentration of the peptide may be conventionally determined as known in the art. For example, the composition according to one aspect of the present invention may comprise the peptide comprising the amino acid sequence of SEQ ID NO: 1, a peptide having at least 80% sequence homology with the amino acid sequence or a fragment thereof at a content of 10 to 1000 mg/L, specifically, 50 to 500 mg/L, and more specifically, 30 to 200 mg/L, but if there is a difference in content-based effect, the content may be suitably adjusted. In another aspect, the composition may comprise the peptide at 1 mg/L or more, 5 mg/L or more, 10 mg/L or more, 20 mg/L or more, 30 mg/L or more, 40 mg/L or more, 50 mg/L or more, 60 mg/L or more, 70 mg/L or more, 80 mg/L or more, or 90 mg/L or more. Also, the composition may comprise the peptide at 50000 mg/L or less, 40000 mg/L or less, 30000 mg/L or less, 200000 mg/L or less, 10000 mg/L or less, 8000 mg/L or less, 6000 mg/L or less, 4000 mg/L or less, 2000 mg/L or less, 1000 mg/L or less, 900 mg/L or less, 800 mg/L or less, 700 mg/L or less, 600 mg/L or less, or 500 mg/L or less. When the composition includes the peptide in the above range or below, it is suitable for exhibiting an effect intended by the present invention and is able to satisfy both stability and safety of the composition. Moreover, the above range may be appropriate in terms of cost-effectiveness.

In the specification, the dose, administration method, and administration cycle of the peptide are widely known in the art, and thus the peptide may be administered according to the standards known in the art depending on the conditions of each patient. A specific dose may be determined by one of ordinary skill in the art, and a daily dose of the peptide may be, specifically, 1 μg/kg/day to 10 g/kg/day, more specifically, 10 μg/kg/day to 100 mg/kg/day, and further more specifically, 50 μg/kg/day to 50 mg/kg/day, but not limited thereto, and may be changed according to various parameters such as age of a subject for administration, a health condition, and complications. For example, the peptide may be locally or intradermally administered into a corresponding site. Daily doses administered right before, during, and right after transplantation may be 1 mg to 10000 mg based on a 60-kg adult. In another aspect, a dose may be 1 mg or more, 5 mg or more, 10 mg or more, 50 mg or more, 100 mg or more, 200 mg or more, 300 mg or more, 400 mg or more, 500 mg or more, 600 mg or more, 700 mg or more, 800 mg or more, 900 mg or more, or 950 mg or more. In another aspect, the dose may be 10000 mg or less, 9000 mg or less, 8000 mg or less, 7000 mg or less, 6000 mg or less, 5000 mg or less, 4000 mg or less, 3000 mg or less, 2000 mg or less, or 1500 mg or less. In the maintenance step after transplantation, the administration may be performed at least once a day for several days, and the time interval may be increased. For example, the administration may be performed at the $1^{st}$, $2^{th}$, $3^{th}$, and $4^{th}$ weeks, and then performed at the $6^{th}$ and $10^{th}$ weeks.

An organ, tissue, a cluster of cells, and/or isolated cells may be extracted from a donor, and transplanted by any method known in the art (the example of the reference document: Oxford Textbook of Surgery, Morris and Malt, Eds., Oxford University Press (1994)). It may be known to those of ordinary skill in the art that extraction and transplantation methods may be changed according to a variety of environments, for example, a type of the organ, tissue, or cell and a type of donor.

The composition disclosed in the specification may be in a solution prepared by dissolving the peptide in a solvent. The solvent may be any one that can be used in the body, for example, a saline, an aqueous solution or a buffer, without limitation. In one aspect, the composition may be a solution that is prepared by adding the peptide disclosed in the specification to any liquid known in the art (the example of the reference document: Oxford Textbook of Surgery, Morris and Malt, Eds., Oxford University Press, 1994), which is suitable for being administered to a patient, or a liquid suitable for maintaining an organ, tissue or cells in vitro. Generally, the liquid may be an aqueous solution. Examples of the solutions may include phosphate buffered saline (PBS), CELSIOR™ solution (a liquid composition for perfusion, reperfusion and preservations of organs manufactured by Institut Georges Lopez, SALR), PERFADEX™ (a lightly buffered colloid-based electrolyte preservation solution for rapid cooling, perfusion and storage of organs in connection with transplantation manufacture by XVIVO Perfusion AB), Collins' solution, citrate solution, and UNIVERSITY OF WISCONSIN™ (UW) solution (a transplantation solution with the composition of 100 mM potassium lactobionate, 25 mM $KH_2PO_4$, 5 mM $MgSO_4$, 30 mM raffinose, 5 mM adenosine, 3 mM glutathione, 1 mM allopurinol, and 50 g/L Hydroxyethyl starch) (Oxford Textbook of Surgery, Morris and Malt, Eds., Oxford University Press, 1994).

One known transplantation solution is the UW solution, which may contain: $KH_2PO_5$ (25 mmol/L), $MgSO_4$ (5 mmol/L), raffinose (30 mmol/L), hydroxyethyl pentafraction starch (50/L), penicillin (200,000 U/L), insulin (40 U/L), dexamethasone (16 mg/dL), K lactobionate (100 mmol/L), glutathione-stimulating hormone (3 mmol/L), adenosine (5 mmol/L), allopurinol (1 mmol/L), Na (25 mmol/L), and K (125 mmol/L).

Another known transplantation solution is a pay-Collins' solution, which may contain: sodium (10 mM), chloride (15 mM), potassium (115 mM), bicarbonate (10 mM), phosphate (50 mM) and glucose (195 mM).

In one aspect of the present invention, a composition for treating and preventing ischemic injury, which comprises a peptide comprising an amino acid sequence of SEQ ID NO: 1, a peptide having at least 80% sequence homology with the amino acid sequence or a fragment thereof as an active ingredient.

The composition according to an aspect of the present invention is a composition administered to a donor and/or recipient in a preparation step before transplantation or a composition administered to a donor and/or recipient in a maintenance step after transplantation, which may comprise a peptide comprising an amino acid sequence of SEQ ID NO: 1, a peptide having at least 80% sequence homology with the amino acid sequence or a fragment thereof at a content of 0.1 μg/mg to 1 mg/mg, specifically, 1 μg/mg to 0.5 mg/mg, and more specifically, 10 μg/mg to 0.1 mg/mg. Within the above range, the composition may be suitable for exhibiting a desired effect of the present invention, may satisfy both stability and safety of the composition, and may be suitable in terms of cost-effectiveness.

The composition according to an aspect of the present invention may be applied to all animals including a human, a dog, a chicken, a pig, a cow, a sheep, a guinea pig, and a monkey.

The composition according to an aspect of the present invention may be a pharmaceutical composition for treating and preventing IR injury, which comprises a peptide comprising an amino acid sequence of SEQ ID NO: 1, a peptide having at least 80% sequence homology with the amino acid sequence or a fragment thereof as an active ingredient. The pharmaceutical composition according to an aspect of the present invention may be orally, intrarectally, transdermally, intravenously, intramuscularly, intraperitoneally, bone marrow, intrathecally, or subcutaneously administered.

Forms for oral administration may be, but are not limited to, tablets, pills, soft or hard capsules, granules, powders, solution, or emulsion. Forms of non-oral administration can be, but not limited to, an injection, drip, lotion, ointment, gel, cream, suspension, emulsion, suppository, patch or spray.

The pharmaceutical composition according to one aspect of the present invention may comprise, as needed, additives, such as diluents, excipients, lubricants, binders, disintegrants, buffers, dispersants, surfactants, coloring agents, aromatics, or sweeteners. The pharmaceutical composition according to one aspect of the present invention may be prepared by a conventional method in the art.

The active ingredient of the pharmaceutical composition according to an aspect of the present invention may vary according to the patient's age, sex, weight, pathology and state, administration route, or prescriber's judgment. Dosage based on such factors may be determined within levels of those of ordinary skill in the an, and a daily dose of the composition administered into a donor and/or recipient in the preparation step before transplantation or the composition administered to a donor and/or recipient in the maintenance step after transplantation may be, for example, 0.1 μg/kg/day to 1 g/kg/day, specifically, 1 μg/kg/day to 10 mg/kg/day, more specifically, 10 μg/kg/day to 1 mg/kg/day, and further more specifically, 50 μg/kg/day to 100 μg/kg/day, but the present invention is not limited thereto. The pharmaceutical composition according to an aspect of the present invention may be administered one to three times a day, but the present invention is not limited thereto.

The composition according to an aspect of the present invention may be a food composition for treating and preventing an IR injury, which comprises a peptide comprising an amino acid sequence of SEQ ID NO: 1, a peptide having at least 80% sequence homology with the amino acid sequence or a fragment thereof as an active ingredient.

The food composition according to one aspect of the present invention may be formulated in the form of, for example, tablets, granules, powder, liquid, and solid, but the present invention is not particularly limited thereto. Each form may be prepared by mixing components conventionally used in the corresponding field as well as the active ingredient according to the form or the purpose of use without difficulty and may produce a synergic effect in combination with other ingredients.

The terms used in the specification are intended to be used to describe specific embodiments, not to limit the present invention. Terms without numbers ahead are not to limit the quantity but to represent the existence of at least one article cited herein. The terms "comprising," "having," "including" and "containing" should be interpreted openly (i.e. "including but not limited to").

Mention of a numerical range replaces mention of individual numbers within the range, and unless cited otherwise, each number is applied to the specification as individually mentioned in the specification. The end values of all the ranges are included in the range and can be combined individually.

All methods mentioned in the specification may be performed in suitable order unless noted otherwise or explicitly contradicted with the context. The use of any one embodiment and all embodiments, or exemplary language (e.g., "such as", "like ~"), unless included in the claims, is used to more clearly describe the present invention, not to limit the scope of the present invention. Any language herein outside of the claims should not be interpreted as necessary for the present invention. Unless defined otherwise, technical and scientific terms used herein have meanings ordinarily understood by those of ordinary skill in the art to which the present invention belongs.

The exemplary embodiments of the present invention include the best mode known to the inventors to perform the present invention. Variations in the exemplary embodiments can become clear to those skilled in the art when reading the descriptions above. It is expected that the inventors suitably use such variations, and embody the present invention by different methods described in the specification. Thus, the present invention, as allowed by the patent law, includes equivalents and all modifications of the gist of the present invention mentioned in the accompanying claims. Moreover, all possible variations with any combination of the above-mentioned components are included in the present invention, unless explicitly stated otherwise or contradicting the context. Although the present invention is described and shown by exemplary embodiments, those skilled in the art will understand well that there can be various changes in the form and details without departing from the spirit of the invention and range, defined by the claims below.

In the following examples, the effects of inhibiting renal injury and enhancing flap survivability were examined by administering the peptide having the sequence set forth in SEQ ID NO: 1 (PEP 1) in IR injuries occurring at the kidney, lung, rectus abdominis flaps, thereby confirming the effects of the peptide on prevention and treatment of an ischemic injury.

EXAMPLES

Hereinafter, the configuration and effects of the present invention will be described in further detail with reference to examples and experimental examples. However, the following examples and experimental examples are merely provided to illustrate the present invention to help understanding the present invention, and the scope of the present invention is not limited thereto.

Example 1: Synthesis of Peptide

The peptide of SEQ ID NO: 1 (hereinafter, referred to as "PEP 1") was prepared according to a conventionally known method of solid phase peptide synthesis. Specifically, the peptide was synthesized by coupling each amino acid from the C-terminus through Fmoc solid phase peptide synthesis (SPPS) using ASP48S (Peptron, Inc., Daejeon, Korea). Peptides in which the first amino acid at the C-terminus is attached to the resin were used as follows:

$NH_2$-Lys(Boc)-2-chloro-Trityl Resin
$NH_2$-Ala-2-chloro-Trityl Resin
$NH_2$-Arg(Pbf)-2-chloro-Trityl Resin In all amino acid ingredients used to synthesize the peptide, the N-term was protected with Fmoc, and the residues were protected with Trt, Boc, t-butylester (t-Bu), and 2,2,4,6,7-pentamethyl dihydro-benzofuran-5-sulfonyl (Pbf) that can be removed from an acid. Examples of the amino acids are as follows:

Fmoc-Ala-OH, Fmoc-Arg(Pbf)-OH, Fmoc-Glu(OtBu)-OH, Fmoc-Pro-OH, Fmoc-Leu-OH, Fmoc-ile-OH, Fmoc-Phe-OH, Fmoc-Ser(tBu)-OH, Fmoc-Thr(tBu)-OH, Fmoc- Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

As a coupling reagent, 2-(1H-Benzotriazole-1-yl)-1,1,3,3-tetamethylaminium hexafluorophosphate (HBTU)/N-Hydroxybenzotriazole (HOBt)/4-Methylmorpholine (NMM) was used. Fmoc deprotection was carried out using piperidine in 20% DMF. To isolate the synthesized peptide from the resin and remove the protective group of the residue, a cleavage cocktail [trifluoroacetic acid (TFA) triisopropylsilane (TIS)/ethanedithiol (EDT)/$H_2O$=92.5/2.5/2.5/2.5] was used.

Each peptide was synthesized by a repeated process of reacting each of corresponding amino acids to the starting amino acid protected by the amino acid protective group while binding to a solid phase scaffold, washing the resulting product with a solvent, and performing deprotection. After being detached from the resin, the synthesized peptide was purified by HPLC, coupling validated by mass spectrometry (MS), and lyophilized.

The purity of all peptides used in the embodiment was 95% or higher by high-performance liquid chromatography.

A specific process for preparing the peptide PEP1 according to the present invention will be described as follows:
1) Coupling The amino acid (8 equivalents) protected with $NH_2$-Lys(Boc)-2-chloro-trityl resin, and a coupling reagent [HBTU (8 equivalents)/HOBt (8 equivalents)/NMM (16 equivalents)] melted in DMF were mixed together and incubated at room temperature for 2 hours. The resulting product was sequentially washed with DMF, MeOH, and DMF.
2) Fmoc Deprotection Piperidine in 20% DMF was added to the resulting product, and the mixture was incubated twice at room temperature for 5 minutes and then sequentially washed with DMF, MeOH and DMF.
3) The peptide backbone [$NH_2$-E(OtBu)-A-R(Pbf)-P-A-L-L-T(tBu)-S(tBu)-R(Pbf)L-R(Pbf)-F-I-P-K(Boc)-2-chloro-Trityl Resin] was prepared by repeating reactions 1 and 2.
4) Cleavage: The peptide was isolated from the resin by adding the cleavage cocktail.
5) After adding cooling diethyl ether to the obtained mixture, a peptide obtained by centrifugation was precipitated.
6) Following purification by Prep-HPLC, a resulting product was analyzed by LC/MS to identify a molecular weight, and lyophilized to prepare a powder.

Example 2: Renal Transplantation

Kidney IR which may occur in renal transplantation was induced as follows for observing the effect of PEP1.

A renal JR injury mouse model was obtained by inducing IR by bilateral clamping renal pedicles for 30 minutes and restoring blood flow after 30 minutes by removing the clamps. Experimental groups were divided into three groups, which are an administered group (PEP 1), a control group (PBS: without PEP 1 administration), and a Sham group (no bilateral clamping). PEP 1 was subcutaneously injected at a concentration of 1000 nmol/kg 30 minutes before and 12 hours after the IR induction.

A C57BL/6 mouse (8-week-old; Charles River Laboratories, Wilmington, Mass.) was used to induce renal IR injury. The renal pedicles were clamped with vascular forceps to block blood flow, and ischemia was induced for 28 hours in the renal IR injury model, followed by reperfusion.

The peptide PEP 1 was diluted with PBS to a concentration of 1000 nmol/kg, and then intraperitoneally injected twice, 30 minutes before and 12 hours after the IR. The experiment was conducted by dividing experimental groups into the administered group (PEP 1), the control group (PBS), and the Sham group (the group without renal injury as the group in which IR injury does not occur).

Experimental Example 1: Protective Effect Against IR Injury-Induced Renal Dysfunction Blood was taken 24 hours after the JR and the levels of blood urea nitrogen (BUN) and creatine as renal toxicity markers were measured, renal tissue was taken and prepared into paraffin blocks for immunohistochemical and histological studies, and then proteins were extracted to measure cytokine levels. The creatine concentration and BUN were measured using an autoanalyzer (Technicon RA-1000; Bayer, Tarrytown, N.Y.).

As a result, the PEP 1-administered group showed significantly decreased BUN and creatine levels, compared with the PBS control group (refer to FIG. 1).

Experimental Example 2: Preventive Effect Against Renal Tissue Injury

Figure 2:
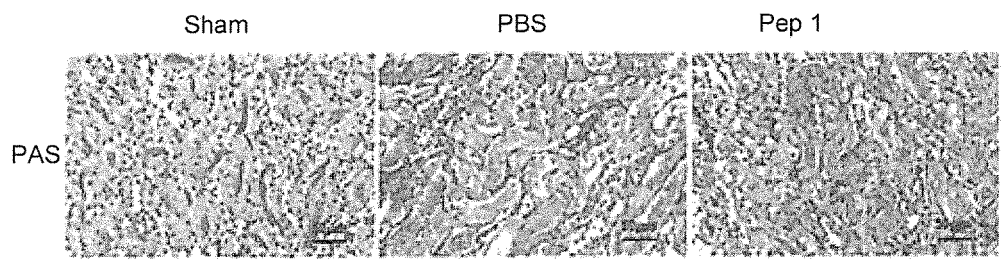
FIG. 2 shows images of renal tissue treated with PAS staining after 24 hours of IR.
Figure 3:
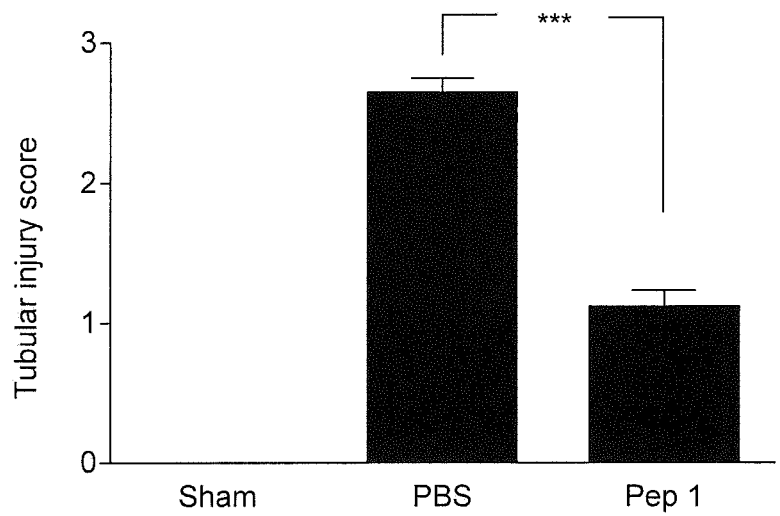
FIG. 3 is a renal tissue injury scoring graph for renal tissue after 24 hours of IR.

Renal tissue was stained with periodic-acid-Schiff (PAS) according to the protocol of the manufacturer (Polysciences, Inc., Warrington, Pa., USA) 24 hours after the IR. After the staining, renal tissue injury was evaluated through renal tissue injury scoring. The PEP 1-administered group showed remarkably increased renal tissue injury, compared with the PBS control group (refer to FIGS. 2 and 3).

Experimental Example 4: Inhibitory Effect Against Renal Apoptosis

Renal apoptosis was evaluated by staining renal tissue with TUNEL stain 24 hours after the IR. Renal paraffin sections were stained with TUNEL using a TUNEL staining kit (Roche Applied Science, Indianapolis, Ind., USA).

Figure 4:
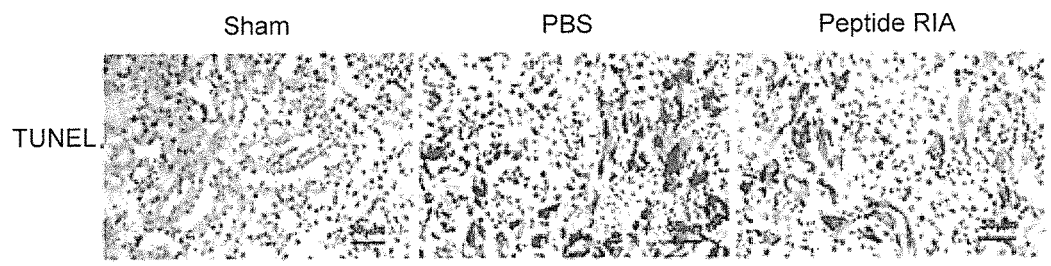
FIG. 4 shows images of renal tissue treated with TUNEL staining after 24 hours of IR.
Figure 5:
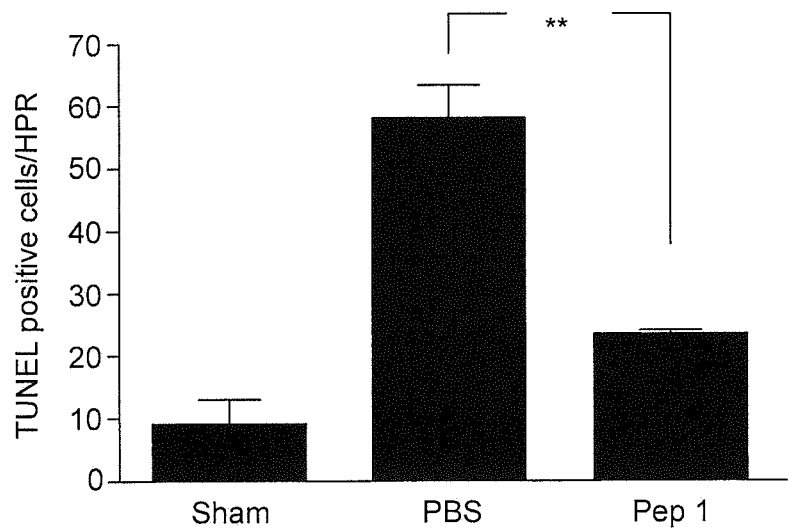
FIG. 5 shows a graph of TUNEL positive cells obtained by evaluating renal tissue through TUNEL staining after 24 hours of IR.

As a result, the PEP 1-administered group showed remarkably decreased TUNEL-positive cells, compared with the PBS control group, indicating that PEP 1 inhibits renal tissue apoptosis (refer to FIGS. 4 and 5).

Experimental Example 5: Inhibitory Effect Against Infiltration of Innate Immune Cells in Renal Tissue Infiltration of innate immune cells was evaluated by staining the renal tissue with a macrophage maker (F4/80) and a neutrophil maker (Gr-1) through immunohistochemistry 24 hours after the IR. Specifically, infiltrated macrophages and neutrophils were stained with a macrophage-specific antibody (F4/80, abcam., Cambridge, Mass.) by an immunochemical method performed on paraffin-containing sections.

Figure 6:
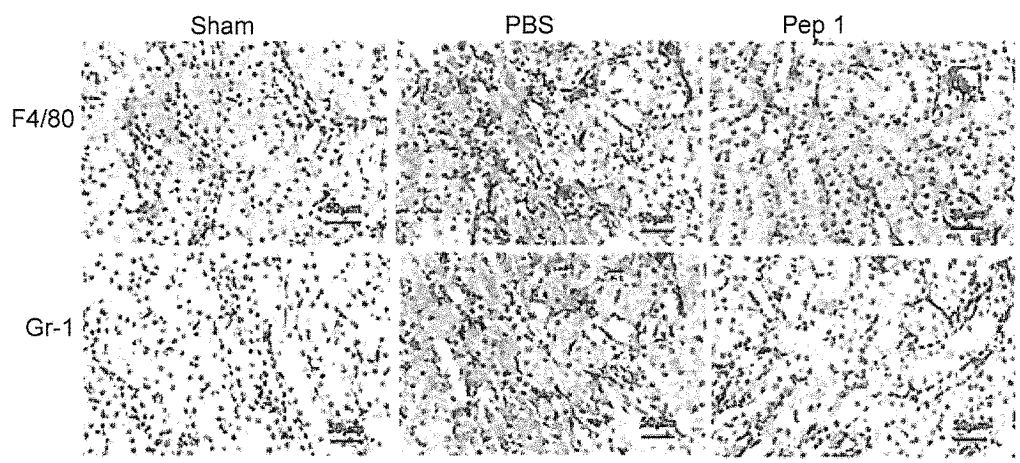
FIG. 6 shows innate immune cell infiltration for renal tissue, evaluated by immunohistochemistry with a macrophage maker (F4/80) and a neutrophil maker (Gr-1) after 24 hours of IR.
Figure 7:
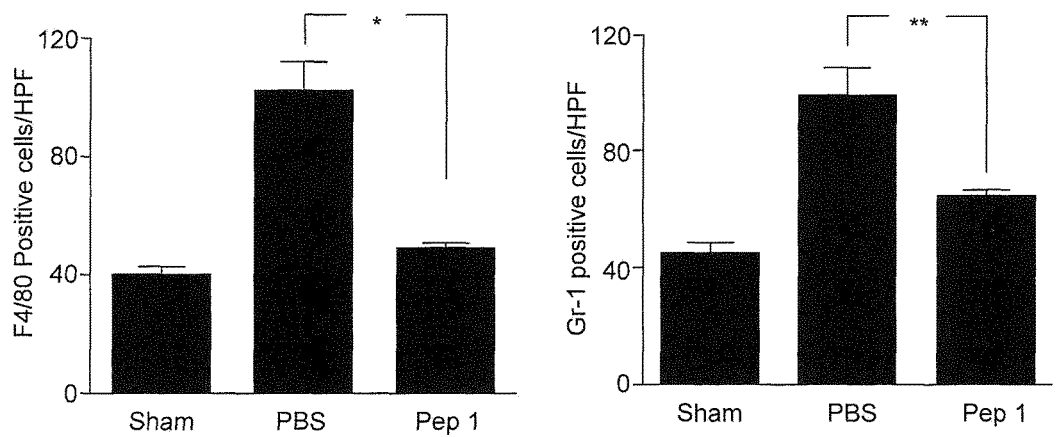
FIG. 7 are graphs showing F4/80 and Gr-1 positive cells for renal tissue after 24 hours of IR.

The PEP 1-administered group showed remarkably decreased infiltration of macrophages and neutrophils into renal tissue, compared with the PBS control group (refer to FIGS. 6 and 7).

Experimental Example 6: Inhibitory Effect Against Secretion of Inflammatory Cytokines Protein was extracted from renal tissue 24 hours after the IR, and IL-6, MCP-1 and TNF-α levels were measured by a cytometric bead array. Mouse IL-6, MCP-1, TNF-α, and an ELISA kit were purchased from R&D Systems, and the experiment was conducted according to the manufacturer's protocol.

Figure 8:
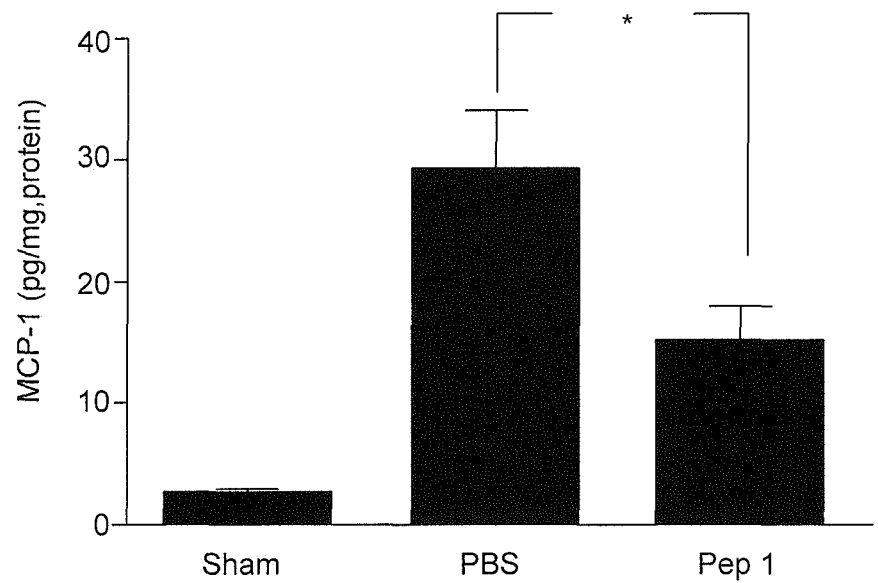
FIGS. 8 to 10 are graphs showing inhibitory effects on secretion of inflammatory cytokines in renal tissue after 24 hours of IR.
Figure 9:
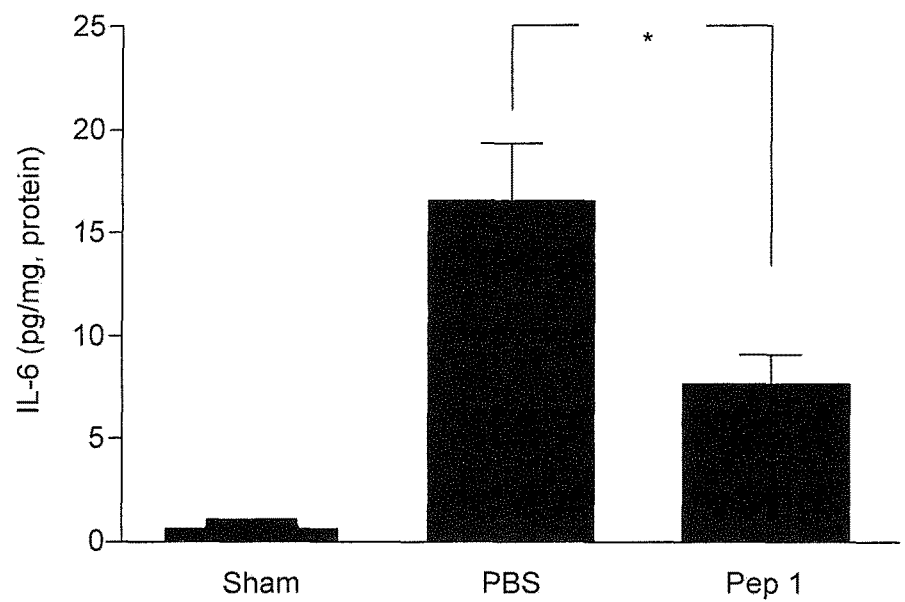
Figure 10:
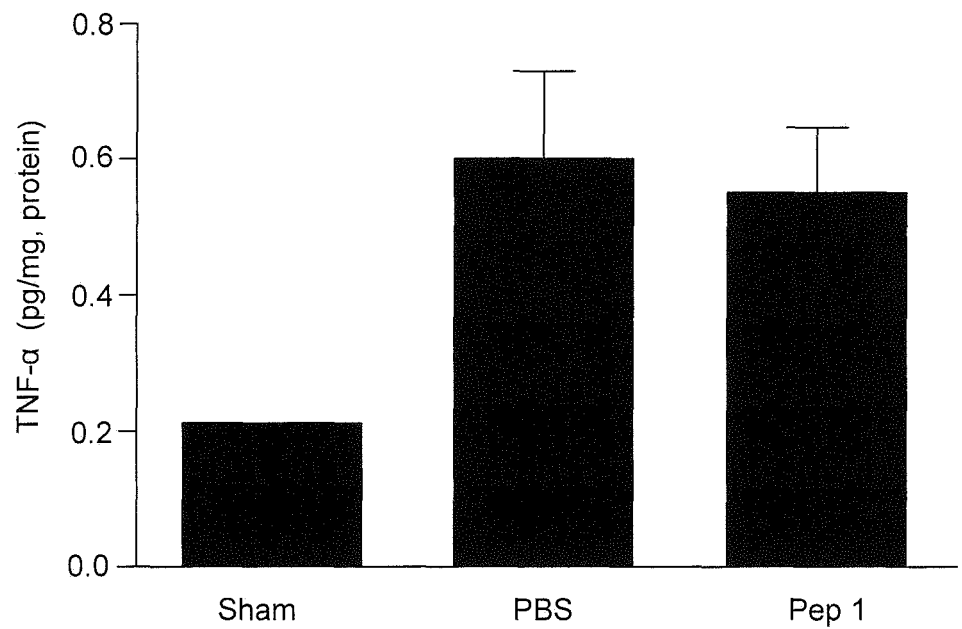

As a result, the PEP 1-administered group showed significantly decreased IL-6 and MCP-1 levels, compared with the PBS control group, but no significant difference in TNF-α level was observed (refer to FIGS. 8 to 10).

As described above, the effect of PEP 1 on protecting the renal IR injury was evaluated by renal failure (BUN, creatine), renal tissue injury (tubular injury), renal apoptosis, immune cell infiltration in the renal tissue, and inhibition of cytokine secretion in the renal tissue.

The IR PBS control group showed increased serum BUN and creatine levels and increased renal tissue injury, compared with the sham group. However, the PEP 1-administered group showed significantly decreased BUN and creatine levels, and decreased renal tissue injury and renal apoptosis, compared with the control group. Also, the PEP 1-administered group showed inhibited infiltration of inflammatory cells (neutrophils and macrophages) caused by IR in the kidney, and significantly inhibited secretion of inflammatory cytokines (interleukin-6 and monocyte chemotactic protein-1), compared with the PBS control group.

Example 3: Flap Transplantation

Figure 11:
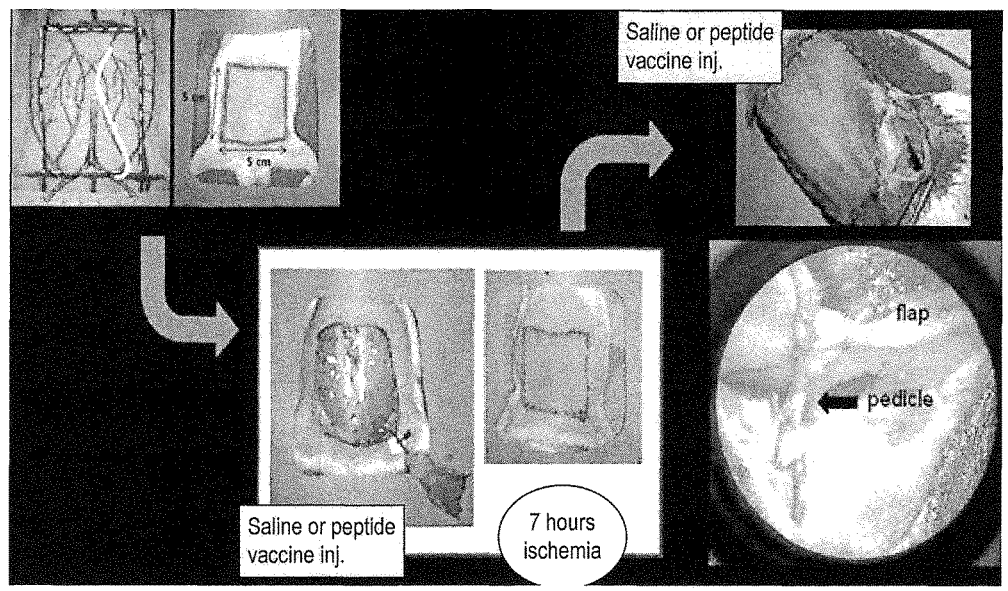
FIG. 11 shows images illustrating a process of inducing IR injury to evaluate flap survivability.

Transplantation of a flap of the rectus abdominis was carried out as follows. An IR injury rat model was obtained by detaching a flap with a size of 5 cm×5 cm from abdominal skin of a white rat (Sprague-Dawley Rat, 180 to 230 g), adding PEP1 or saline to the rat, inducing ischemia through clamping, and restoring blood flow after 7 hours by removing the clamps (refer to FIG. 11).

Experimental groups were divided into three groups, which are an administered group (PEP 1), a control group (PBS without PEP 1), and a sham group (group in which no IR injury induced). PEP 1 (10 mg/500 μl) or saline (500 Id) was intramuscularly injected 30 minutes before and 1, 2, 3, 4, 5, and 7 days after the IR induction.

Flap survivability was measured 7 days after the IR induction. The flap survivability was measured through digital image analysis using imageJ program.

Figure 12:
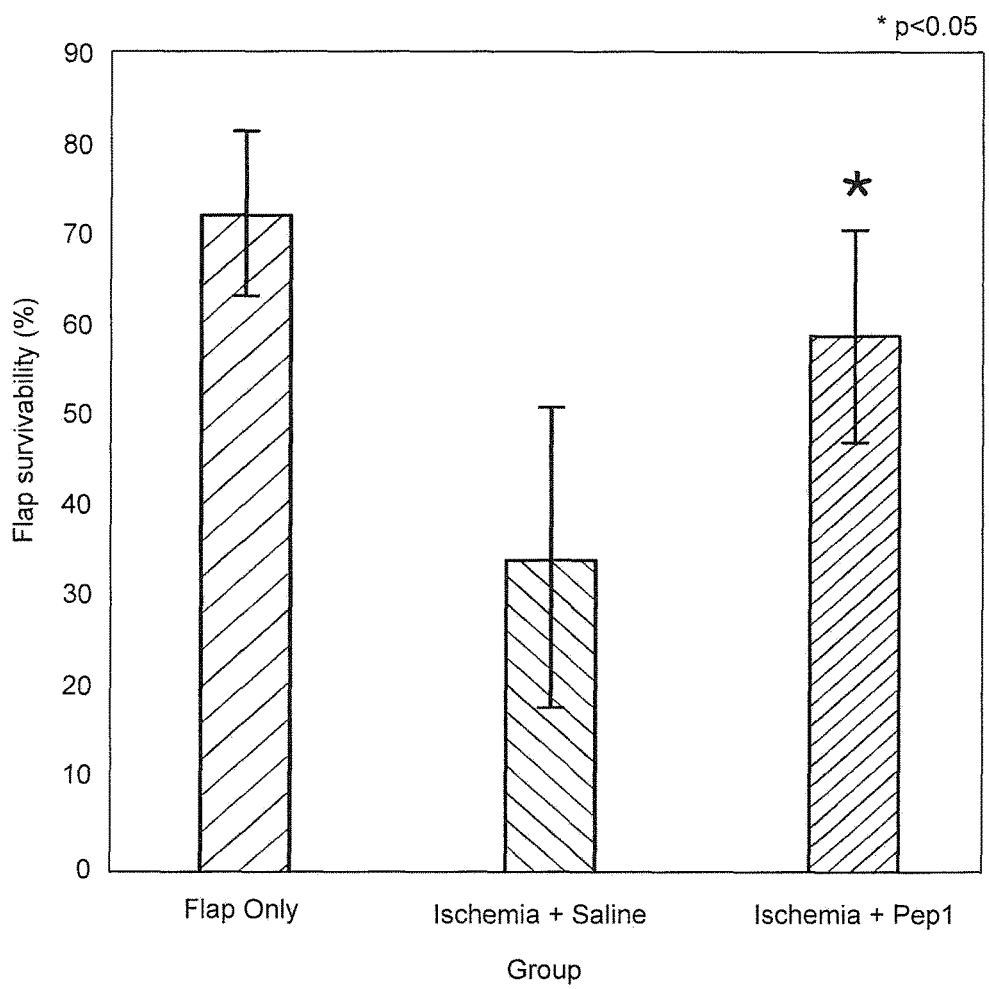
FIG. 12 is a graph of flap viability of a PEP-treated group and a saline-treated group 7 days after IR induction.
Figure 13:
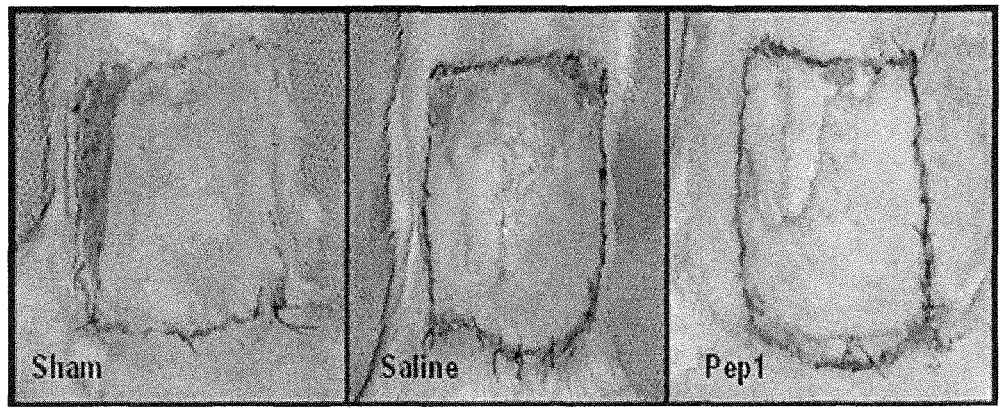
FIG. 13 shows digital images obtained using ImageJ program.

According to the measurement 7 days after the IR induction, the flap survivability was 34.69%±16.44% in the saline-treated group, and 58.88%±11.44% in the PEP1-treated group, which was higher than that in the saline-treated group (refer to FIG. 12). A statistical significance ($p<0.05$) was found between the groups.

Example 4: Lung Transplantation

A lung transplantation model for examining an effect of PEP1 on preventing IR injury was set as follows.

The experiment was performed using two rats with the same gene, and lung transplantation was carried out by detaching the left lung from a donor rat and placing the donor's lung in the left thoracic cavity from which an original left lung was removed of the recipient rat. To basically prevent rejection, the rats had the same gene. Both the donor rat and recipient rat had weights of 300 to 350 g, and were the Sprague-Dawley species. Following the extraction of a lung from the donor rat, the lung was transplanted to the recipient rat through surgical procedures.

The lung extraction from the donor rat was performed as follows.

① A mixture of rompun:zoletil (1:2, 1 ml/kg) was intraperitoneally injected into the white rat (donor).

② Following tracheotomy, a tube with a 16-gauge intravenous catheter was intubated and connected to a ventilator (Harvard Rodent Ventilator Model; Harvard Apparatus CO, Holliston, Mass.) (Vt=10 ml/kg, PEEP=2 cm H2O, respiratory rate=80/min). Mechanical ventilation was carried out with 100% oxygen.

③ Following laprotomy and median sternotomy, 300 IU heparin was injected into the inferior vena cava.

An 18-gauge angio-catheter was inserted into the main pulmonary artery through the right ventricular outflow, and 50 mL normal saline was injected under 20 cm $H_2O$ pressure at 10° C. through the main pulmonary artery catheter while the inferior vena cava was divided in the abdominal cavity, and the left atrium was divided. During perfusion, mechanical ventilation was continuously performed to allow uniform lung perfusion.

④ Following the perfusion, trachea was ligated while the lung expanded under the endotracheal intubation, a heart-lung block was extracted, and then peripheral structures such as esophagus were removed on a cold petri-dish. The heart-lung block was weighed, and subjected to cold storage in a perfusion solution, which was the same as the lung perfusion solution. Ischemic duration was set three hours.

The lung to be transplanted was prepared as follows.

① The extracted lung was placed on a petri-dish containing a cold flush solution, covered with a wet sponge, and then equipped with cuffs. This procedure was performed under hypothermia.

② After ensuring a sufficient distance for connecting cuffs, the cuffs were attached to a 18 G catheter for the pulmonary artery, a 16 G catheter for the pulmonary vein, and a 16 G catheter for bronchus using 4-0 silk.

Transplant surgery was performed as follows:

① The recipient rat was sedated by intraperitoneal injection, and after tracheotomy, a tube with a 16-gauge intravenous catheter was intubated, and fixed with 4-0 silk. As for the donor, mechanical ventilation was carried out.

② Incisions of the pectoralis major and the latissimus dorsi in the right decubitus position, posterolateral thoracotomy was made through the bed of the fourth rib.

③ After cutting the left pulmonary ligament, the left lung was lifted out of the rib cage and held, and then a pulmonary hilum was dissected to expose the pulmonary artery, the pulmonary vein, and the left main stem bronchus.

④ All of the three structures were clamped with microvascular clips (Micro-Serrefine, Fine Science Tools, Foster city, CA).

⑤ The left lung was removed, and the pulmonary artery, pulmonary vein, and bronchus of the transplanted lung were sutured using a cuff technique.

For the experiment, the lung transplant rats were divided into four groups. To determine a suitable concentration of PEP1, each of low concentration (5 mg) and high concentration (50 mg) of PEP1 were administered into a lung of the donor rat before transplantation, a lung extracted from the donor, and the recipient after transplantation.

① 50 mL normal saline-administered group.

② PERFADEX™ (a lightly buffered colloid-based electrolyte preservation solution for rapid cooling, perfusion and storage of organs in connection with transplantation manufacture by XVIVO Perfusion AB) 50 mL administered group.

③ PERFADEX™ (a lightly buffered colloid-based electrolyte preservation solution for rapid cooling, perfusion and storage of organs in connection with transplantation manufacture by XVIVO Perfusion AB) 50 mL+PEP1 5 mg administered group.

④ PERFADEX™ (a lightly buffered colloid-based electrolyte preservation solution for rapid cooling, perfusion and storage of organs in connection with transplantation manufacture by XVIVO Perfusion AB) 50 mL+PEP1 50 mg administered group.

To evaluate the function of transplanted lung after transplantation, the following experiments were performed.

Experimental Example 1: Hematoxylin & Eosin Staining (H&E Staining)

When lung injury occurs due to IR injury, hemorrhage occurs, and the alveolar wall is thickened. To measure a degree of the IR injury occurring when the above-mentioned four solutions were used as lung preservation solutions with respect to hemorrhage and a thickness of the alveolar wall, H & E staining was performed as follows.

The intermediate area of the transplanted lung was fixed with formalin, subjected to H & E staining, and then alveolar tissue samples were compared between the groups through optical microscopy.

Figure 14:
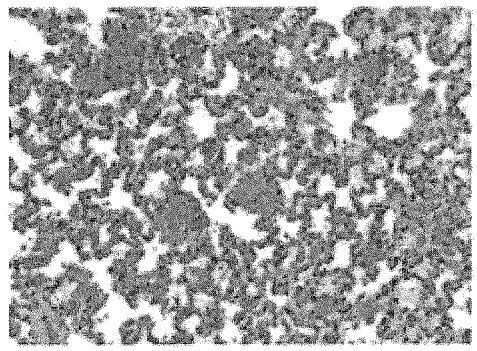
FIG. 14 shows images of alveolar tissue observed using an optical microscope after the intermediate part of the transplanted lung is fixed with formalin, and treated with hematoxylin & eosin (H&E) staining, when i) normal saline, ii) PERFADEX™ (a lightly buffered colloid-based electrolyte preservation solution for rapid cooling, perfusion and storage of organs in connection with transplantation manufacture by XVIVO Perfusion AB), iii) PERFADEX™ (a lightly buffered colloid-based electrolyte preservation solution for rapid cooling, perfusion and storage of organs in connection with transplantation manufacture by XVIVO Perfusion AB) and PEP1 5 mg, and iv) PERFADEX™ (a lightly buffered colloid-based electrolyte preservation solution for rapid cooling, perfusion and storage of organs in connection with transplantation manufacture by XVIVO Perfusion AB) and PEP1 50 mg are used as lung preservation solutions used in lung transplantation of rats.
Figure 14:
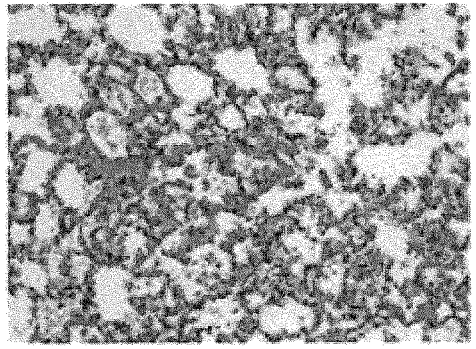
Figure 14:
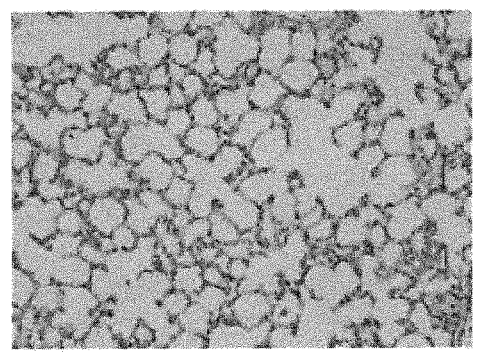
Figure 14:
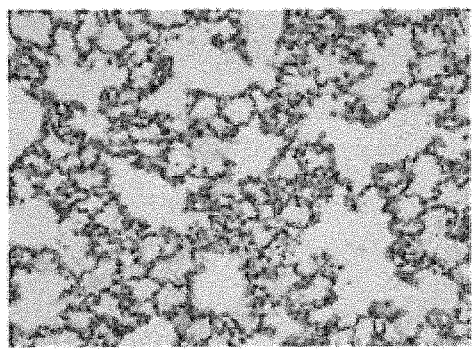

The analysis showed that hemorrhage and the thickness of the alveolar wall increased in the order of the normal saline group (① group), the PERFADEX™ (a lightly buffered colloid-based electrolyte preservation solution for rapid cooling, perfusion and storage of organs in connection with transplantation manufacture by XVIVO Perfusion AB) group (② group), the PERFADEX™ (a lightly buffered colloid-based electrolyte preservation solution for rapid cooling, perfusion and storage of organs in connection with transplantation manufacture by XVIVO Perfusion AB) & PEP1 50 mg group (④ group), and the PERFADEX™ (a lightly buffered colloid-based electrolyte preservation solution for rapid cooling, perfusion and storage of organs in connection with transplantation manufacture by XVIVO Perfusion AB) & PEP1 5 mg group (③ group). Particularly, when the PERFADEX™ (a lightly buffered colloid-based electrolyte preservation solution for rapid cooling, perfusion and storage of organs in connection with transplantation manufacture by XVIVO Perfusion AB) & PEP1 5 mg group (③ group) was used as a lung preservation solution, hemorrhage rarely occurred, and the alveolar wall did not get harder. This shows that, when 5 mg PEP1, rather than 50 mg PEP1, was added to PERFADEX™ (a lightly buffered colloid-based electrolyte preservation solution for rapid cooling, perfusion and storage of organs in connection with transplantation manufacture by XVIVO Perfusion AB), it is more effective in preventing hemorrhage and in maintaining the alveolar wall, which indicate higher IR injury inhibitory effects. (refer to FIG. 14)

Experimental Example 2: Measurement of Wet/Dry Weight Ratio

The lower lobe of the transplanted lung was cut and weighed, dried in an oven at 60° C. for 24 hours, and then weighed again.

The analysis showed that reperfusion edema was increased in the order of the normal saline administered group (① group), the PERFADEX™ (a lightly buffered colloid-based electrolyte preservation solution for rapid cooling, perfusion and storage of organs in connection with transplantation manufacture by XVIVO Perfusion AB) & PEP1 50 mg administered group (④ group), the PERFADEX™ (a lightly buffered colloid-based electrolyte preservation solution for rapid cooling, perfusion and storage of organs in connection with transplantation manufacture by XVIVO Perfusion AB) administered group (② group), the PERFADEX™ (a lightly buffered colloid-based electrolyte preservation solution for rapid cooling, perfusion and storage of organs in connection with transplantation manufacture by XVIVO Perfusion AB) & PEP1 5 mg administered group (③ group).

Figure 15:
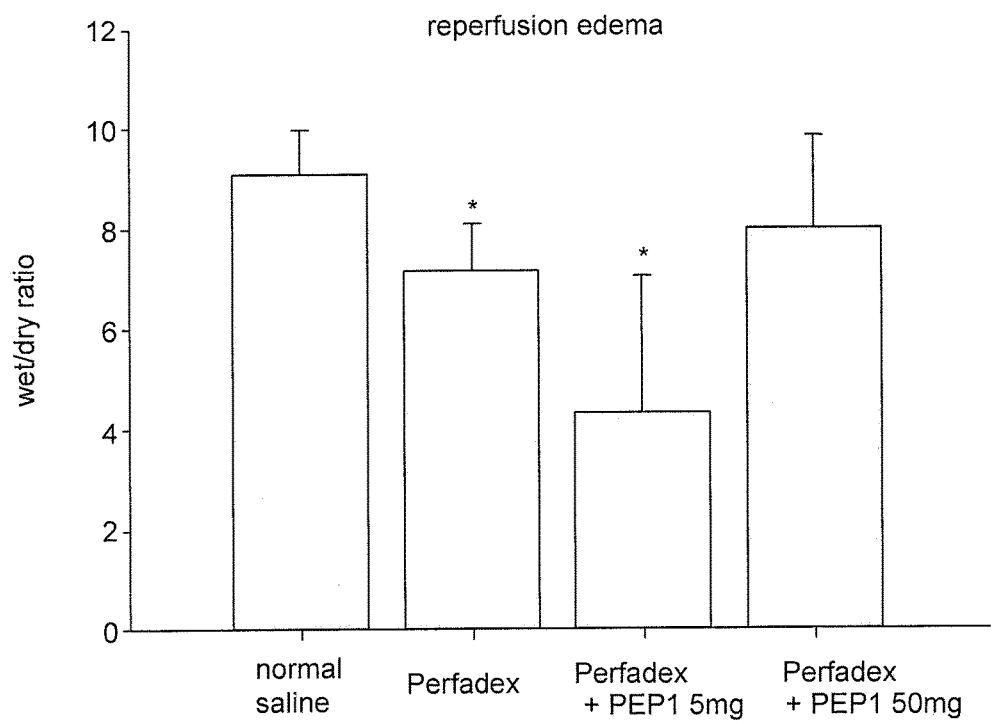
FIG. 15 is a graph showing a weight of a lower lobe in the transplanted lung, which, after lung transplantation in a rat, is cut out and weighed after an experiment, dried in a 60° C. drier for 24 hours, and then weighed again.

PERFADEX™ (a lightly buffered colloid-based electrolyte preservation solution for rapid cooling, perfusion and storage of organs in connection with transplantation manufacture by XVIVO Perfusion AB) administered group (② group) and the PERFADEX™ (a lightly buffered colloid-based electrolyte preservation solution for rapid cooling, perfusion and storage of organs in connection with transplantation manufacture by XVIVO Perfusion AB) & PEP1 5 mg administered group (③ group) showed significantly ($p<0.05$) decreased reperfusion edema, compared with the normal saline administered group (① group), and the PERFADEX™ (a lightly buffered colloid-based electrolyte preservation solution for rapid cooling, perfusion and storage of organs in connection with transplantation manufacture by XVIVO Perfusion AB) & PEP1 5 mg administered group (③ group) showed the lowest level. (refer to FIG. 15)

Experimental Example 3: Analysis of Bronchoalveolar Lavage Fluid (BAL)

5 mL normal saline was instillated into the bronchus, and then extracted to be used in an analysis of neutrophil contents.

Figure 16:
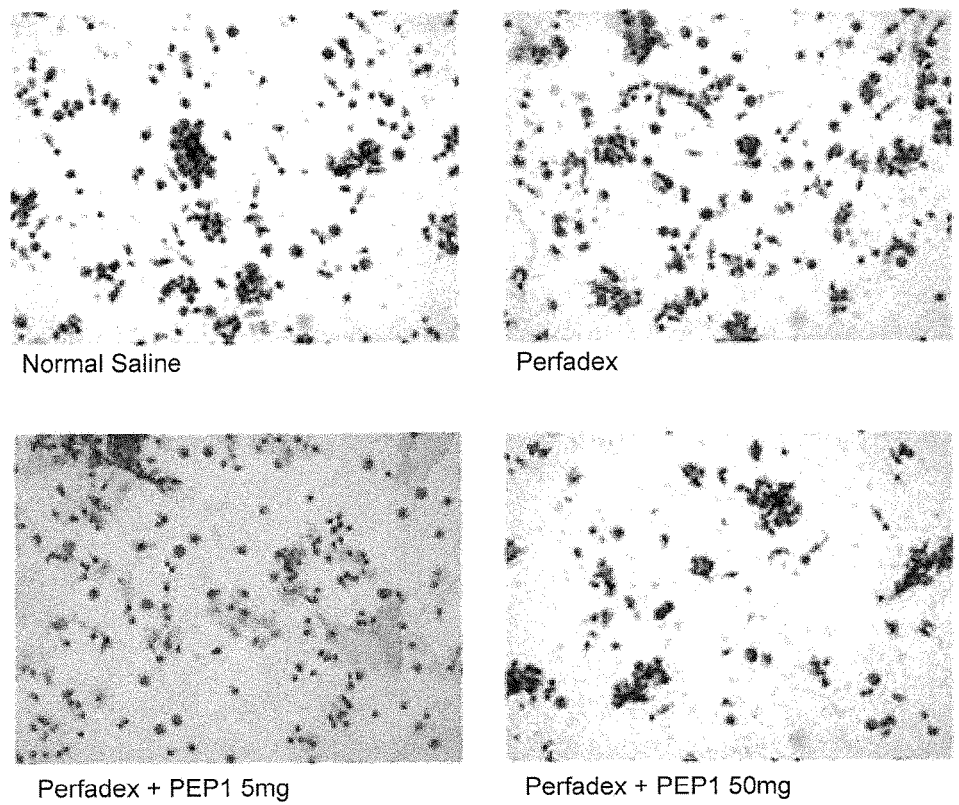
FIG. 16 shows images of neutrophil contents, which are analyzed through endotracheal instillation of 5 mL normal saline and extraction after lung transplantation in rats.

The analysis showed that rates of inflammatory cells in the BAL were increased in the order of the normal saline administered group (① group), the PERFADEX™ (a lightly buffered colloid-based electrolyte preservation solution for rapid cooling, perfusion and storage of organs in connection with transplantation manufacture by XVIVO Perfusion AB) administered group (② group), the PERFADEX™ (a lightly buffered colloid-based electrolyte preservation solution for rapid cooling, perfusion and storage of organs in connection with transplantation manufacture by XVIVO Perfusion AB) & PEP1 50 mg administered group (④ group), and the PERFADEX™ (a lightly buffered colloid-based electrolyte preservation solution for rapid cooling, perfusion and storage of organs in connection with transplantation manufacture by XVIVO Perfusion AB) & PEP1 5 mg administered group (③ group). Arrows indicate inflammatory cells. It was seen that the PERFADEX™ (a lightly buffered colloid-based electrolyte preservation solution for rapid cooling, perfusion and storage of organs in connection with transplantation manufacture by XVIVO Perfusion AB) & PEP1 5 mg administered group (③ group) showed the lowest expression of inflammatory cells (refer to FIG. 16).

What is claimed is:

1. A method for organ, tissue or cell transplantation comprising isolating an organ, tissue or cell for transplantation from a donor; contacting the isolated organ, tissue or cells with the isolated peptide of SEQ ID NO: 1; and transplanting the isolated organ, tissue, or cell into a recipient.

2. A method for organ, tissue or cell transplantation comprising administering to a donor and/or recipient for organ, tissue or cell transplantation the isolated peptide of SEQ ID NO: 1; isolating an organ, tissue or cell for transplatation from the donor; and transplanting the isolated organ, tissue, or cell into the recipient.

3. The method of claim 2 wherein the peptide is administered in any one or more stages before, after, or during transplantation to the donor or to the recipient.

4. The method of claim 3 comprising administering the peptide through perfusion of an organ, tissue or cells in a donor's or recipient's body with the organ, tissue or cells present in the body.

5. The method according to claim 2 wherein the peptide is administered in a single dose of 1 to 10000 mg based on a 60-kg adult.

6. The method according to claim 2 wherein the daily dose of the administered peptide is 1 µg/kg/day to 10 g/kg/day.

7. A method for organ, tissue or cell transplantation comprising isolating an organ, tissue or cell for transplantation from a donor; contacting the isolated organ, tissue or cells with a composition comprising the isolated peptide of SEQ ID NO: 1; and transplanting the isolated organ, tissue, or cell into a recipient.

8. The method of claim 7 wherein the composition comprises a sufficient amount of the peptide as the active ingredient to strengthen the survivability or function of the organ, tissue, or cells after transplantation into a recipient.

9. The method of claim 8 wherein the composition comprises 10 to 1000 mg/L of the isolated peptide.

10. The method of claim 9 wherein the composition comprises 50 to 500 mg/L of the isolated peptide.

11. The method of claim 7 wherein the composition further comprises phosphate buffered saline (PBS), Collins' solution, and citrate solution.

12. A method for organ, tissue or cell transplantation comprising administering to a donor and/or recipient for organ, tissue or cell transplantation a composition comprising the isolated peptide of SEQ ID NO: 1; isolating an organ, tissue or cell for transplantation from the donor; and transplanting the isolated organ, tissue, or cell into the recipient.

13. The method of claim 12 wherein the composition is administered in any one or more stages before, after, or during transplantation to the donor or to the recipient.

14. The method of claim 12 wherein the composition is administered through oral, intrarectal, transdermal, intravenous, intramuscular, intraperitoneal, bone marrow, intrathecal, or subcutaneous routes.

* * * * *

UNITED STATES PATENT AND TRADEMARK OFFICE
CERTIFICATE OF CORRECTION

PATENT NO. : 10,662,223 B2  
APPLICATION NO. : 15/307632  
DATED : May 26, 2020  
INVENTOR(S) : Kim

Page 1 of 1

It is certified that error appears in the above-identified patent and that said Letters Patent is hereby corrected as shown below:

On the Title Page

Item (72), in "Inventors", Line 1, delete "Seoul" and insert -- Gangnam-gu, Seoul --, therefor.

In the Claims

In Column 27, Claim 2, Line 12, delete "transplatation" and insert -- transplantation --, therefor.

Signed and Sealed this  
Fourth Day of August, 2020

Andrei Iancu  
*Director of the United States Patent and Trademark Office*